United States Patent
Adachi et al.

(10) Patent No.: US 12,427,228 B2
(45) Date of Patent: Sep. 30, 2025

(54) MENISCUS REGENERATION MATERIAL

(71) Applicants: HIROSHIMA UNIVERSITY, Hiroshima (JP); SANYO CHEMICAL INDUSTRIES, LTD., Kyoto (JP)

(72) Inventors: Nobuo Adachi, Hiroshima (JP); Naosuke Kamei, Hiroshima (JP); Masakazu Ishikawa, Hiroshima (JP); Tomoyuki Nakasa, Hiroshima (JP); Shingo Kawabata, Kyoto (JP); Tsubasa Yamanaka, Kyoto (JP)

(73) Assignees: HIROSHIMA UNIVERSITY, Hiroshima (JP); SANYO CHEMICAL INDUSTRIES, LTD., Kyoto (JP)

( * ) Notice: Subject to any disclaimer, the term of this patent is extended or adjusted under 35 U.S.C. 154(b) by 995 days.

(21) Appl. No.: 17/282,577

(22) PCT Filed: Sep. 25, 2019

(86) PCT No.: PCT/JP2019/037589
§ 371 (c)(1),
(2) Date: Apr. 2, 2021

(87) PCT Pub. No.: WO2020/071208
PCT Pub. Date: Apr. 9, 2020

(65) Prior Publication Data
US 2021/0338890 A1   Nov. 4, 2021

(30) Foreign Application Priority Data
Oct. 5, 2018 (JP) .................................. 2018-190168

(51) Int. Cl.
*A61K 38/16* (2006.01)
*A61K 35/32* (2015.01)
*A61L 27/22* (2006.01)
*A61L 27/36* (2006.01)
*A61P 19/02* (2006.01)
*A61P 19/04* (2006.01)
*C07K 14/435* (2006.01)
*C07K 14/78* (2006.01)

(52) U.S. Cl.
CPC .......... *A61L 27/3654* (2013.01); *A61K 35/32* (2013.01); *A61K 38/16* (2013.01); *A61L 27/227* (2013.01); *A61L 27/3612* (2013.01); *A61P 19/02* (2018.01); *A61P 19/04* (2018.01); *C07K 14/43586* (2013.01); *C07K 14/78* (2013.01); *A61L 2300/252* (2013.01); *A61L 2300/412* (2013.01); *A61L 2430/06* (2013.01)

(58) Field of Classification Search
CPC ........ A61K 38/16; A61K 35/32; C07K 14/78; C07K 14/435; A61L 27/3654
See application file for complete search history.

(56) References Cited

U.S. PATENT DOCUMENTS

| | | | |
|---|---|---|---|
| 6,033,654 A | 3/2000 | Stedronsky et al. | |
| 6,380,154 B1 | 4/2002 | Cappello et al. | |
| 10,130,675 B2 | 11/2018 | Kawabata | |
| 2005/0202069 A1 | 9/2005 | Kurokawa et al. | |
| 2007/0092492 A1 | 4/2007 | Matsuda et al. | |
| 2011/0060412 A1* | 3/2011 | Semler .............. | A61K 38/1841 623/14.12 |
| 2016/0106801 A1 | 4/2016 | Kawabata | |
| 2017/0058001 A1 | 3/2017 | Kim | |

FOREIGN PATENT DOCUMENTS

| | | |
|---|---|---|
| CN | 103370089 | 10/2013 |
| CN | 105073125 | 11/2015 |
| CN | 106659149 | 5/2017 |
| CN | 107496990 | 12/2017 |
| CN | 108404205 | 8/2018 |
| EP | 1 656 946 | 5/2006 |
| EP | 2 676 683 | 9/2016 |
| JP | H06-9373 | 1/1994 |
| JP | H09-509840 | 10/1997 |
| JP | H10-80438 | 3/1998 |
| JP | 2002-145797 | 5/2002 |
| JP | 2004-24864 | 1/2004 |
| JP | 2004-49921 | 2/2004 |
| JP | 2004-339395 | 12/2004 |
| JP | 2006-150072 | 6/2006 |
| JP | 2007-528755 | 10/2007 |
| JP | 2008-1763 | 1/2008 |

(Continued)

OTHER PUBLICATIONS

Huang et al., Expert Opin. Drug Deliv., 2015, vol. 12(5):779-791.*
Dr. Ying-Chen Chen et al., "Development and Characterization of Acellular Extracellular Matrix Scaffolds from Porcine Menisci for Use in Cartilage Tissue Engineering" Tissue Engineering,: Part C, vol. 21, No. 9, (2015), pp. 971-986.
International Search Report issued Nov. 26, 2019 in International (PCT) Application No. PCT/JP2019/037589.
Kano, Toshiya et al., "Creation of next-generation meniscus treatment using thermo-sensitive gel (silk-elastin)", The Journal of Japanese Orthopedic Surgical Society, Aug. 2018, vol. 92, No. 8, p. S1867, ISSN 0021-5325, col. 2-4-12, with English Translation.
Kawabata, Shingo, "Creation of treatment technology for meniscus injury", Sanyo Kasei News, vol. 2019 summer, No. 515, 2019, pp. 1-4, ISSN 0036-4649, with English Translation.

(Continued)

*Primary Examiner* — Xiaozhen Xie
(74) *Attorney, Agent, or Firm* — Wenderoth, Lind & Ponack, L.L.P.

(57) ABSTRACT

The present invention provides a meniscus regeneration material having high meniscus regeneration ability. The meniscus regeneration material includes protein (A), which has a total percentage of β-turns and random coils of 60 to 85% as determined by circular dichroism spectroscopy, and the meniscus regeneration material may further include meniscus tissue fragment (B). The present invention also provides the use of the meniscus regeneration material for promoting meniscus regeneration and treating meniscus damage, cartilage defects, or osteoarthritis.

3 Claims, No Drawings
Specification includes a Sequence Listing.

(56) References Cited

FOREIGN PATENT DOCUMENTS

| | | | | |
|---|---|---|---|---|
| JP | 2008-125916 | 6/2008 | | |
| JP | 2009-508540 | 3/2009 | | |
| JP | 2012-236112 | 12/2012 | | |
| JP | 2013-176547 | 9/2013 | | |
| JP | 2013-208425 | 10/2013 | | |
| JP | 2014-530698 | 11/2014 | | |
| JP | 2015-63517 | 4/2015 | | |
| JP | 2016-216453 | 12/2016 | | |
| JP | 2017-186264 | 10/2017 | | |
| JP | 2018-861 | 1/2018 | | |
| JP | 2018-000957 | 1/2018 | | |
| JP | 6339459 | 5/2018 | | |
| JP | 6338259 | 6/2018 | | |
| JP | 2018-154578 | 10/2018 | | |
| KR | 10-1446503 | 9/2014 | | |
| WO | 95/23611 | 9/1995 | | |
| WO | 98/10063 | 3/1998 | | |
| WO | 2007/002362 | 1/2007 | | |
| WO | 2007/020449 | 2/2007 | | |
| WO | 2007/038837 | 4/2007 | | |
| WO | WO-2012111438 A1 * | 8/2012 | ......... | A61L 26/0028 |
| WO | 2012/172887 | 12/2012 | | |
| WO | 2013/057497 | 4/2013 | | |

OTHER PUBLICATIONS

Kawaguch, Hiroshi, "International and National Guidelines of Osteoarthritis Treatment", Japanese Journal of Joint Diseases, 2016, vol. 35, No. 1, pp. 1-9, with English Abstract.

International Search Report and Written Opinion issued Jan. 12, 2021 in International (PCT) Application No. PCT/JP2020/044316.

Poursaid, A. et al., "In situ gelling silk-elastinlike protein polymer for transarterial chemoembolization", Biomaterials (2015), vol. 57, pp. 142-152.

Qiu, W. et al., "Wet-Spinning of Recombinant Silk-Elastin-Like Protein Polymer Fibers with High Tensile Strength and High Deformability", Biomacromolecules (2009), vol. 10, pp. 602-608.

International Search Report issued Jul. 16, 2019 in International (PCT) Application No. PCT/JP2019/018606.

Shenje, L. et al., "Lineage tracing of cardiac explant derived cells", PLoS One (Apr. 2008), vol. 3, No. 4: e1929 doi:10.1371/journal.pone.0001929 (Year: 2008), 2 pages.

Majid, Q. et al., "Natural Biomaterials for Cardiac Tissue Engineering: A Highly Biocompatible Solution", Front. Cardivasc. Med. 7:554597, pp. 1-32 Oct. 2020.

Chaudhuri, R. et al., "Biomaterials and cells for cardiac tissue engineering: Current choices", Materials Science and Engineering C, vol. 79, pp. 950-957 (Year: 2017).

Suzuki, K. et al., "Targeted Cell Delivery Into Infarcted Rat Hearts by Retrograde Intracoronary Infusion: Distribution, Dynamics, and Influence on Cardiac Function", Circulation (Sep. 14, 2004), pp. II-225 to II-230.

Hart, D. et al., "Thermally Associating Polypeptides Designed for Drug Delivery Produced by Genetically Engineered Cells" J. Pharm. Sci., vol. 96, pp. 484-516 (Year: 2006).

Sreerama, N. et al., "Estimation of Protein Secondary Structure from Circular Dichroism Spectra: Comparison of CONTIN, SELCON, and CDSSTR Methods with an Expanded Reference Set", Analytical Biochemistry, vol. 287 (2000), pp. 252-260.

The Chemical Society of Japan, Shin Jikken Kagaku Koza 20 Seibutsu Kagaku I, (1978) pp. 14-19, 26-31, 54-57.

Written Opinion of the International Searching Authority issued May 20, 2014 in International (PCT) Application No. PCT/JP2014/054026.

Office Action issued Apr. 23, 2025 in related U.S. Appl. No. 17/781,280.

Haider et al., "Molecular Engineering of Silk-Elastinlike Polymers for Matrix-Mediated Gene Delivery: Biosynthesis and Characterization", Molecular Pharmaceutics, 2005, vol. 2, No. 2, pp. 139-150.

* cited by examiner

MENISCUS REGENERATION MATERIAL

TECHNICAL FIELD

The present invention relates to meniscus regeneration materials.

BACKGROUND ART

Osteoarthritis (OA) is the most common type of "arthritis" among elderly people. According to 2011 statistics, 25,300,000 people suffer from OA (Non-Patent Literature 1), and about 8,000,000 of them have pain or other symptoms. Knee OA is classified into primary OA and secondary OA. Primary OA is caused by factors related to aging, whereas secondary OA is caused by another disease, such as traumatic cartilage defect, meniscus damage, or anterior cruciate ligament damage. In particular, meniscus damage is considered as a trigger of knee OA, attracting worldwide attention.

Knee OA therapies so far focus on the regeneration of defective parts of joint cartilage. Various therapeutic methods have been developed and implemented (Patent Literature 1). However, when joint cartilage alone is repaired without repairing meniscus, good conditions are very difficult to maintain. Thus, a combination of a meniscus repair/regeneration therapy and alignment correction is essential for an ultimate radical cure of knee OA.

Meniscus is a very important tissue in knee joints not only for impact absorption and stabilization of the joints but also for smooth movement of the joints. The meniscus has extremely low repairability because it histologically consists of fibrocartilage in which blood vessels are scarce as in joint cartilage. Since the meniscus bears a high mechanical load, once damaged, the meniscal tissue is very difficult to repair. The most common treatment for severe symptoms (e.g., scraping feeling and pain) is arthroscopic partial meniscectomy, a symptomatic therapy. Repair and regeneration of damaged tissues are very difficult at present. Meanwhile, under the slogan of "Save the Meniscus," a worldwide effort to repair meniscus by meniscus suture techniques is being made for knee OA prevention. However, 30% of suture surgery patients need a surgery again, suggesting a limitation of therapies of deformed meniscus which has low self-curing ability. To overcome the issue, advanced therapies are studied and developed. Examples include regenerative medicine involving the transplantation of autologous cultured synovium stem cells and collagen-containing graft materials for meniscus (Patent Literature 2). Yet, compared to cartilage damage, there is a very limited selection of therapies for meniscus damage. New approaches to cure meniscus damage are awaited.

CITATION LIST

Patent Literature

Patent Literature 1: JP 6338259 B
Patent Literature 2: JP 2012-236112 A

Non-Patent Literature

Non-Patent Literature 1: International and National Guidelines of Osteoarthritis Treatment, Japanese Journal of Joint Diseases, 35(1): 1-9, 2016

SUMMARY OF INVENTION

Technical Problem

The present invention aims to provide a meniscus regeneration material having high meniscus regeneration ability.

Solution to Problem

As a result of intensive studies to achieve the aim, the present inventors arrived at the present invention. Specifically, the present invention relates to a meniscus regeneration material including a protein (A), wherein
the protein (A) contains at least one of a polypeptide chain (Y) and a polypeptide chain (Y');
a total number of the polypeptide chain (Y) and the polypeptide chain (Y') in the protein (A) is 1 to 100;
the polypeptide chain (Y) includes 2 to 200 tandem repeats of at least one amino acid sequence (X) selected from the group consisting of an amino acid sequence VPGVG (1) set forth in SEQ ID No: 1, an amino acid sequence GVGVP (4) set forth in SEQ ID No: 4, an amino acid sequence GPP, an amino acid sequence GAP, and an amino acid sequence GAHGPAGPK (3) set forth in SEQ ID No: 3;
the polypeptide chain (Y') includes the polypeptide chain (Y) in which 5% or less of amino acid residues are replaced by at least one of a lysine residue and an arginine residue, and a total number of the lysine residue and the arginine residue is 1 to 100;
the protein (A) has a total percentage of β-turns and random coils of 60 to 85% as determined by circular dichroism spectroscopy; and
when the amino acid sequence (X) in which 60% or less of amino acid residues are replaced by at least one of a lysine residue and an arginine residue is denoted as an amino acid sequence (X'), a ratio of a total number of amino acid residues in the amino acid sequence (X) and the amino acid sequence (X') in the protein (A) to the number of all amino acid residues in the protein (A) is 50 to 70%.

Advantageous Effects of Invention

The meniscus regeneration material of the present invention has excellent meniscus regeneration ability and enables normal meniscus regeneration.

DESCRIPTION OF EMBODIMENTS

The meniscus regeneration material of the present invention includes a protein (A). The protein (A) contains at least one of a polypeptide chain (Y) and a polypeptide chain (Y'). The total number of the polypeptide chain (Y) and the polypeptide chain (Y') in the protein (A) is 1 to 100. The polypeptide chain (Y) includes 2 to 200 tandem repeats of at least one amino acid sequence (X) selected from the group consisting of an amino acid sequence VPGVG (1) set forth in SEQ ID No: 1, an amino acid sequence GVGVP (4) set forth in SEQ ID No: 4, an amino acid sequence GPP, an amino acid sequence GAP, and an amino acid sequence GAHGPAGPK (3) set forth in SEQ ID No: 3. The polypeptide chain (Y') includes the polypeptide chain (Y) in which 5% or less of amino acid residues are replaced by at least one of a lysine residue and an arginine residue, and a total number of the lysine residue and the arginine residue is 1 to 100. The protein (A) has a total percentage of β-turns and random coils of 60 to 85% as determined by circular dichroism spectroscopy. When the amino acid sequence (X) in which 60% or less of amino acid residues are replaced by at least one of a lysine residue and an arginine residue is denoted as an amino acid sequence (X'), a ratio of a total number of amino acid residues in the amino acid sequence (X) and the amino acid sequence (X') in the protein (A) to the number of all amino acid residues in the protein (A) is 50 to 70%.

The meniscus regeneration material of the present invention includes a protein (A). The protein (A) contains at least one of a polypeptide chain (Y) and a polypeptide chain (Y'). Such a material can maintain an appropriate wet state of a gel described in detail later.

The polypeptide chain (Y) may include one type or two or more types of the amino acid sequence (X).

To maintain an appropriate wet state of a gel described in detail later and to enhance the meniscus regeneration ability, preferred examples of the amino acid sequence (X) include a VPGVG sequence (1) and a GVGVP sequence (4).

Specific examples of the polypeptide chain (Y) include a $(VPGVG)_b$ sequence, a $(GVGVP)_c$ sequence, and a $(GAHGPAGPK)_d$ sequence. The symbols b, c, and d each represent the number of tandem repeats of the amino acid sequence (X), and the number is an integer of 2 to 200.

When the protein (A) contains a plurality of the polypeptide chains (Y) in one molecule, the polypeptide chains (Y) may be the same as or different from each other. The protein (A) may contain one sequence selected from the group consisting of a $(VPGVG)_b$ sequence, a $(GVGVP)_c$ sequence, and a $(GAHGPAGPK)_d$ sequence, or two or more of the sequences.

When the protein (A) contains a plurality of the polypeptide chains (Y), the polypeptide chains (Y) have the same number or different numbers of tandem repeats of the amino acid sequence (X). Specifically, the protein (A) may contain a plurality of the polypeptide chains (Y) having the same or different number (b, c, or d) of tandem repeats of the amino acid sequence (X).

To maintain an appropriate wet state of a gel described in detail later, preferred examples of the polypeptide chain (Y) include a $(VPGVG)_b$ sequence and a $(GVGVP)_c$ sequence.

The polypeptide chain (Y) includes 2 to 200 tandem repeats of the amino acid sequence (X) (i.e. each of b, c, and d represents an integer of 2 to 200). To maintain an appropriate wet state of a gel, the number of the tandem repeats of the amino acid sequence (X) is preferably 2 to 100 (i.e. each of b, c, and d represents an integer of 2 to 100), still more preferably 2 to 50 (i.e. each of b, c, and d represents an integer of 2 to 50), particularly preferably 2 to 40 (i.e. each of b, c, and d represents an integer of 2 to 40).

The polypeptide chain (Y') includes the polypeptide chain (Y) in which 5% or less of amino acid residues are replaced by at least one of a lysine residue and an arginine residue, and the total number of the replacing lysine residue and the replacing arginine residue is 1 to 100.

Identification of the polypeptide chain (Y') is made based on whether the polypeptide chain Y is obtained when all of lysine (K) residues and arginine (R) residues in the sequence of the protein (A) are replaced by other amino acid residues (glycine (G), alanine (A), valine (V), proline (P) or histidine (H)).

To maintain an appropriate wet state of a gel described in detail later, the percentage of the at least one of the replacing lysine residue and the replacing arginine residue in the polypeptide chain (Y') is preferably 0.06 to 5%, more preferably 0.5 to 5%, particularly preferably 1 to 5%.

The polypeptide chain (Y') may contain an amino acid sequence (X') that is the amino acid sequence (X) in which 60% or less of amino acid residues are replaced by at least one of a lysine residue and an arginine residue.

The polypeptide chain (Y') may include one type or two or more types of the amino acid sequence (X) and/or one type or two or more types of the amino acid sequence (X').

Specific examples of the amino acid sequence (X') include an amino acid sequence GKGVP (7) set forth in SEQ ID No: 7, an amino acid sequence GKGKP (8) set forth in SEQ ID No: 8, an amino acid sequence GKGRP (9) set forth in SEQ ID No: 9, and an amino acid sequence GRGRP (10) set forth in SEQ ID No: 10.

To maintain a meniscus-defected face in an appropriate wet state, the amino acid sequence (X') preferably includes at least one sequence selected from the group consisting of the GKGVP sequence (7), the GKGKP sequence (8), and the GRGRP sequence (10), and still more preferably includes the GKGVP sequence (7) and/or the GKGKP sequence (8).

The total number of the polypeptide chain (Y) and the polypeptide chain (Y') in one molecule of the protein (A) is 1 to 100. The total number is preferably 1 to 80, more preferably 1 to 60.

When the total number of the polypeptide chain (Y) and the polypeptide chain (Y') in one molecule of the protein (A) is within the range, an appropriate wet state of a gel described in detail later can be maintained.

When the protein (A) contains the polypeptide chains (Y) each having a different amino acid sequence (X) and/or a different number of tandem repeats of the amino acid sequence (X), the number of the polypeptide chains (Y) refers to the total number of the polypeptide chains (Y) each counted as one. The same applies to the polypeptide chain (Y').

In the meniscus regeneration material of the present invention, a percentage of the total number of amino acid residues in the amino acid sequence (X) and the amino acid sequence (X') in the protein (A) in the number of all amino acid residues in the protein (A) is 50 to 70%.

The material in which the percentage is lower than 50% does not easily become a gel as described in detail later. The material in which the percentage is higher than 70% does not dissolve well in water.

To enhance the meniscus regeneration ability, the percentage is preferably 52.5 to 67.5%, more preferably 55 to 65%.

The percentage may be determined with a protein sequencer, specifically by the following measurement method.

<Determination of Percentage of Total Number of Amino Acid Residues in Amino Acid Sequence (X) and Amino Acid Sequence (X') in the Number of all Amino Acid Residues in Protein (A)>

The protein (A) is divided into fragments of about not more than 30 amino acid residues using two or more techniques which can cleave the sequence at specific amino acid residues. Next, the fragments are separated by high-performance liquid chromatography (HPLC), and then the amino acid sequences are analyzed with a protein sequencer. The complete amino acid sequence of the protein (A) is determined by peptide mapping of the amino acid sequence obtained. Then, a percentage of the total number of amino acid residues in all the amino acid sequences (X) and amino acid residues in all the amino acid sequences (X') in the number of all amino acid residues in the protein (A) is calculated using the following equation:

Percentage (%) of total number of amino acid residues in all amino acid sequences($X$) in protein($A$) and amino acid residues in all amino acid sequences($X'$) in protein ($A$)=

100×[{number of amino acid sequences($X$)}×{number of amino acid residues in amino acid sequence($X$)}+{number of amino acid sequences($X'$)}×{number of amino acid residues in amino acid sequence($X'$)}]/{number of all amino acid residues in protein($A$)}

To control the total percentage of the β-turns and the random coils in the protein (A), which are described later, within a prescribed range, to maintain an appropriate wet state of a gel, and to enhance the meniscus regeneration ability, the protein (A) preferably contains a polypeptide chain (S) including 2 to 50 tandem repeats of a GAGAGS sequence (2).

To maintain an appropriate wet state of a gel, the number of the tandem repeats of the GAGAGS sequence (2) in the polypeptide chain (S) is preferably 2 to 40, more preferably 2 to 30, particularly preferably 2 to 10.

To enhance the meniscus regeneration ability, the percentage of the number of the amino acid residues in all the GAGAGS sequences (2) in the protein (A) in the number of all amino acid residues in the protein (A) [100×{number of GAGAGS sequences (2) in protein (A)×6}/{number of all amino acid residues in protein (A)}] is preferably 5 to 50%, more preferably 10 to 47.5%, particularly preferably 20 to 45%.

The percentage of the number of the amino acid residues in all the GAGAGS sequences (2) in the number of all amino acid residues in the protein (A) can be determined with a protein sequencer. Specifically, the percentage is determined by the following measurement method.

<Percentage of the Number of Amino Acid Residues in all GAGAGS Sequences (2) in Protein (A) in the Number of all Amino Acid Residues in Protein (A)>

The protein (A) is divided into fragments of about not more than 30 amino acid residues using two or more techniques which can cleave the sequence at specific amino acid residues. Next, the fragments were separated by high-performance liquid chromatography (HPLC), and then the amino acid sequence is analyzed with a protein sequencer. The complete amino acid sequence of the protein (A) is determined by peptide mapping of the amino acid sequence obtained. Then, a percentage of the number of the amino acid residues in all the GAGAGS sequences (2) in the protein (A) in the number of all amino acid residues in the protein (A) is calculated using the following equation:

Percentage of number of amino acid residues in all GAGAGS sequences(2) in protein($A$) in the number of all amino acid residues in protein($A$) (%)=[{number of GAGAGS sequences(2)×6}/{number of all amino acid residues in protein($A$)}]×100

In the case where the protein (A) contains total two or more of at least one polypeptide chain selected from the group consisting of a polypeptide chain (Y), a polypeptide chain (Y'), and a polypeptide chain (S), it may contain an intervening amino acid sequence (Z) between the polypeptide chains. The intervening amino acid sequence (Z) refers to a peptide sequence which consists of one amino acid residue or two or more amino acid residues linked to each other and is not any one of the GAGAGS sequence (2), the amino acid sequence (X), and the amino acid sequence (X'). To maintain an appropriate wet state of a gel described in detail later, the number of amino acid residues in the intervening amino acid sequence (Z) is preferably 1 to 30, more preferably 1 to 15, particularly preferably 1 to 10. Specific examples of the intervening amino acid sequence (Z) include an amino acid sequence VAAGY (11) set forth in SEQ ID No: 11, an amino acid sequence GAAGY (12) set forth in SEQ ID No: 12, and a LGP sequence.

To maintain an appropriate wet state of a gel described in detail later, the percentage of the amino acid residues in all the intervening amino acid sequence(s) (Z) in the number of all amino acid residues in the protein (A) [100×Σ{(number of amino acid residues in intervening amino acid sequence (Z))×(number of intervening amino acid sequences (Z))}/{number of all amino acid residues in protein (A)}] is preferably 0 to 25%, more preferably 0 to 22.5%, particularly preferably 0.01 to 15%.

From the standpoint of degradability in vivo, the protein (A) may contain a terminal amino acid sequence (T) at an end thereof, other than the GAGAGS sequence (2), the amino acid sequence (X), the amino acid sequence (X'), and the intervening amino acid sequence (Z). The terminal amino acid sequence (T) may be present at one end or both ends of the protein (A).

The terminal amino acid sequence (T) does not include a purification tag described later.

The protein (A) preferably has an end structure where the terminal amino acid sequence (T) is linked to the polypeptide chain (Y). The terminal amino acid sequence (T) refers to a peptide sequence which consists of one amino acid residue or two or more amino acid residues linked to each other and is not any one of the GAGAGS sequence (2), the amino acid sequence (X), and the amino acid sequence (X'). From the standpoint of degradability in vivo, the number of amino acid residues in the terminal amino acid sequence (T) is preferably 1 to 100, more preferably 1 to 50, particularly preferably 1 to 40. Specific examples of the terminal amino acid sequence (T) include an amino acid sequence MDPVVLQRRDWENPGVTQLNRLAAHPPFASDPM (13) set forth in SEQ ID No: 13.

From the standpoint of degradability in vivo, the percentage of the number of amino acid residues in the terminal amino acid sequence (T) in the number of all amino acid residues in the protein (A) is preferably 0 to 25%, more preferably 0 to 22.5%, particularly preferably 0.01 to 15%.

The protein (A) may be produced by a biotechnological approach using bacteria as described later. In this case, the protein (A) may include a protein or peptide (hereinafter referred to as "purification tag") having, at the N terminal or C terminal, a specific amino acid sequence other than the terminal amino acid sequence (T) to facilitate the purification or detection of the expressed protein (A). An affinity purification tag is used as the purification tag. Examples of the purification tag include 6×His tag containing polyhistidine, V5 tag, Xpress tag, AU1 tag, T7 tag, VSV-G tag, DDDDK tag, S tag, CruzTag09™, CruzTag22™, CruzTag41™, Glu-Glu tag, Ha.11 tag, and KT3 tag.

Exemplary combinations of a purification tag (i) and a ligand (ii) capable of recognizing and binding to the tag are listed below.
- (i-1) glutathione-S-transferase (GTS) and (ii-1) glutathione
- (i-2) maltose-binding protein (MBP) and (ii-2) amylose
- (i-3) HQ tag and (ii-3) nickel
- (i-4) Myc tag and (ii-4) anti-Myc antibody
- (i-5) HA tag and (ii-5) anti-HA antibody
- (i-6) FLAG tag and (ii-6) anti-FLAG antibody
- i-7) 6×His tag and (ii-7) nickel or cobalt The purification tag sequence may be added by incorporating a nucleic acid encoding the purification tag into the 5' or 3' end of a nucleic acid encoding the protein (A) in an expression vector or using a commercial vector designed to add the purification tag, for example.

From the standpoint of degradability in vivo, the percentage of a sum of the number of amino acid residues in all the intervening amino acid sequence(s) (Z) in the protein (A), the number of amino acid residues in all the terminal amino acid sequence(s) (T) in the protein (A), and the number of amino acid residues in the purification tag in the number of all amino acid residues in the protein (A) is preferably 0 to 25%, more preferably 0 to 22.5%, particularly preferably 0.01 to 15%.

To maintain a defected face in an appropriate wet state, in the case where the protein (A) contains the polypeptide chain (S) in addition to the at least one of the polypeptide chain (Y) and the polypeptide chain (Y'), preferably the polypeptide chain (Y) or the polypeptide chain (Y') and the polypeptide chain (S) are alternately linked by a chemical bond.

The ratio of the number of the GAGAGS sequence (2) to the total number of the amino acid sequence (X) and the amino acid sequence (X') (number of GAGAGS sequence (2):total number of amino acid sequence (X) and amino acid sequence (X')) is preferably 1:1.5 to 1:20, more preferably 1:1.5 to 1:6, particularly preferably 1:2 to 1:5 to give a moderate total percentage of the β-turns and the random coils in the protein (A).

Some preferred examples of the protein (A) are listed below.
- (A1): a protein in which the amino acid sequence (X) is the GVGVP sequence (4);
- (A11): a protein containing a polypeptide chain (Y'1) having an amino acid sequence which includes 2 to 200 tandem repeats of the GVGVP sequence (4) and in which one amino acid residue is replaced by a lysine (K) residue;
- (A11-1): a protein containing the polypeptide chain (Y'1) and a polypeptide chain (S1) including 2 to 200 tandem repeats of the GAGAGS sequence (2);
- (A11-2): a protein containing an amino acid sequence $(GVGVP)_4GKGVP(GVGVP)_3$ (6) set forth in SEQ ID No: 6 (Y'11) in which one amino acid residue in a polypeptide chain (Y11) having an amino acid sequence (GVGVP)$ (14) set forth in SEQ ID No: 14 including 8 tandem repeats of a GVGVP sequence (4) is replaced by a lysine (K) residue and the polypeptide chain (S1) including 2 to 200 tandem repeats of the GAGAGS sequence (2); and
- (A11-2-1): a protein containing a polypeptide chain (S1-1) having an amino acid sequence $(GAGAGS)_4$ (5) set forth in SEQ ID No: 5 including 4 tandem repeats of the GAGAGS sequence (2) and a $(GVGVP)_4GKGVP(GVGVP)_3$ sequence (6).

Specific examples include the following proteins:
- (i) a protein (SELP8K) having an amino acid sequence (16) set forth in SEQ ID No: 16 having a molecular mass of about 80 kDa. The sequence (16) includes 12 $(GAGAGS)_4$ sequences (5) and 13 $(GVGVP)_4GKGVP(GVGVP)_3$ sequences (6), which are alternately linked by a chemical bond, and an amino acid sequence $(GAGAGS)_2$ (15) set forth in SEQ ID No: 15 linked by a chemical bond to the linked sequences;
- (ii) a protein (SELP0K) having an amino acid sequence (17) set forth in SEQ ID No: 17 having a molecular mass of about 82 kDa. The sequence (17) has a structure in which 17 $(GAGAGS)_2$ sequences (15) and 17 $(GVGVP)_4GKGVP(GVGVP)_3$ sequences (6) are alternately linked by a chemical bond;
- (iii) a protein (SELP8K4) having an amino acid sequence (29) set forth in SEQ ID No: 29 having a molecular mass of about 30 kDa and including 4 $(GAGAGS)_4$ sequences (5) and 4 $(GVGVP)_4GKGVP(GVGVP)_3$ sequences (6), which are alternately linked by a chemical bond;
- (A11-3): a protein containing a polypeptide chain (Y'12) having an amino acid sequence $(GVGVP)_6GKGVP(GVGVP)_5$ (18) set forth in SEQ ID No: 18 in which one amino acid residue in a polypeptide chain including 12 tandem repeats of the GVGVP sequence (4) is replaced by lysine (K) and the polypeptide chain (S1) including 2 to 200 tandem repeats of the GAGAGS sequence (2);
- (A11-3-1): a protein having an amino acid sequence $(GAGAGS)_4$ (19) set forth in SEQ ID No: 19 including 4 tandem repeats of the GAGAGS sequence (2) and a $(GVGVP)_6GKGVP(GVGVP)_5$ sequence (18);
- (i) a protein having an amino acid sequence (20) set forth in SEQ ID No: 20 having a molecular mass of about 105 kDa. The sequence (20) includes 12 $(GAGAGS)_4$ sequences (19) and 13 $(GVGVP)_6GKGVP(GVGVP)_5$ sequences (18), which are alternately linked by a chemical bond, and the $(GAGAGS)_2$ sequence (15) linked by a chemical bond to the linked sequences;
- (A2): a protein in which the amino acid sequence (X) is the VPGVG sequence (1);
- (A21): a protein containing a polypeptide chain (Y2) including 2 to 200 tandem repeats of the VPGVG sequence (1) and the GAGAGS sequence (2);
- (i) a protein (ELP1.1) having an amino acid sequence (26) set forth in SEQ ID No: 26 having a molecular mass of about 200 kDa. The sequence (26) includes 40 GAGAGS sequences (2), 40 amino acid sequences $(VPGVG)_4$ (24) set forth in SEQ ID No: 24, and 40 amino acid sequences $(VPGVG)_8$ (25) set forth in SEQ ID No: 25, which are arranged such that 40 blocks each consisting of one $(VPGVG)_4$ sequence (24), one GAGAGS sequence (2), and one $(VPGVG)_8$ sequence (25) bound in said order are linked by a chemical bond; and
- (A3): a protein containing the polypeptide chain (Y1) including 2 to 200 tandem repeats of the GVGVP sequence (4) and the polypeptide chain (S1) including 2 to 200 tandem repeats of the GAGAGS sequence (2).

Specific examples also include the following protein:
(i) a protein (SELP6.1) having an amino acid sequence (23) set forth in SEQ ID No: 23 having a molecular mass of about 110 kDa. The sequence (23) includes 5 amino acid sequences (GAGAGS)$_8$ (21) set forth in SEQ ID No: 21 and 5 amino acid sequences (GVGVP)$_{40}$ (22) set forth in SEQ ID No: 22, which are alternately linked by a chemical bond.

Preferred among these are the protein (SELP8K) having the sequence (16), the protein (SELP0K) having the sequence (17), the protein having the sequence (20), the protein (SELP6.1) having the sequence (23), the protein (ELP1.1) having the sequence (26), or the protein (SELP8K4) having the sequence (29).

Examples of the protein (A) also include proteins each having an amino acid sequence which is not less than 70% identical to the amino acid sequence of the protein (SELP8K) having the sequence (16), the protein (SELP0K) having the sequence (17), the protein having the sequence (20), the protein (SELP6.1) having the sequence (23), the protein (ELP1.1) having the sequence (26), or the protein (SELP8K4) having the sequence (29).

The percentage of identicalness is preferably not less than 80%, more preferably not less than 90%.

The protein (A) in the present invention has a total percentage of β-turns and random coils of 60 to 85% as determined by circular dichroism spectroscopy. Proteins having an identical sequence may have different total percentages of β-turns and random coils depending on, for example, the methods of producing the proteins, the methods of purifying the proteins, the pH of solvents for dissolving the proteins, or the polarities of the solvents.

The protein (A) having the total percentage of 1-turns and random coils of lower than 60% does not dissolve well in water. The protein having the total percentage of higher than 85% does not easily becomes a gel as described in detail later.

To maintain a defected face in an appropriate wet state and promote meniscus regeneration, the total percentage of β-turns and random coils in the protein (A) is preferably 65 to 80%, more preferably 70 to 75%.

The percentage can be controlled by any method and can be increased or decreased by the following methods.

Examples of the method to increase the percentage include a dilution refolding method (high dilution method) in which a single protein (A) is diluted with excess buffer and then refolded.

Examples of the method to reduce the percentage include modifying the protein (A) with a denaturant, heat, or the like.

The total percentage of β-turns and random coils in the protein (A) is determined by the following measurement.
<Measurement of Total Percentage of β-Turns and Random Coils in Protein (A)>

The protein is dissolved in deionized water (4° C.) to a concentration of 0.3 mg/mL to prepare an aqueous solution of the protein. The aqueous solution of the protein is measured with a circular dichroism spectrometer (JASCO Corporation, J-820) at a measurement temperature of 4° C. The percentage of β-turns and the percentage of random coils are calculated using a secondary structure analysis program (JWSSE model, JASCO Corporation), and the sum of the percentages is determined as a total percentage of β-turns and random coils.

From the standpoint of degradability in vivo, the protein (A) has a molecular mass as determined by SDS-PAGE (SDS polyacrylamide gel electrophoresis) of preferably 15 to 200 kDa, more preferably 30 to 150 kDa, particularly preferably 70 to 120 kDa.

To enhance the meniscus regeneration ability, the protein (A) in the present invention has a hydrophobicity of preferably 0.2 to 1.2, more preferably 0.4 to 1.0, particularly preferably 0.42 to 0.80.

The hydrophobicity of the protein (A) refers to a degree of hydrophobicity of a protein (A) molecule. The hydrophobicity can be calculated by inserting the number ($M_\alpha$) of each amino acid residue in one molecule of the protein (A), the hydrophobicity ($N_\alpha$) of each amino acid residue, and the total number ($M_T$) of amino acid residues in one molecule of the protein (A) in the equation below. The hydrophobicities of the amino acid residues are below-mentioned values described in a non-patent literature (Albert L. Lehninger, David L. Nelson, Lehninger, Principles of Biochemistry, Vol. 1, Hirokawa Shoten Co., September, 2010, pp. 346-347).

$$\text{Hydrophobicity} = \Sigma(M_\alpha \times N_\alpha)/(M_T)$$

$M_\alpha$: number of each amino acid residue in one molecule of artificial protein (A)
$N_\alpha$: hydrophobicity of the amino acid residue
$M_T$: total number of amino acid residues in one molecule of artificial protein (A)
A (alanine): 1.8
R (arginine): −4.5
N (asparagine): −3.5
D (aspartic acid): −3.5
C (cysteine): 2.5
Q (glutamine): −3.5
E (glutamic acid): −3.5
G (glycine): −0.4
H (histidine): −3.2
I (isoleucine): 4.5
L (leucine): 3.8
K (lysine): −3.9
M (methionine): 1.9
F (phenylalanine): 2.8
P (proline): −1.6
S (serine): −0.8
T (threonine): −0.7
W (tryptophan): −0.9
Y (tyrosine): −1.3
V (valine): 4.2

For example, the hydrophobicity of an artificial protein (A) having the (GVGVP)$_4$GKGVP(GVGVP)$_3$ sequence (6) is calculated as follows:

$$\text{Hydrophobicity of artificial protein}(A) = \{16(\text{number of } G) \times (-0.4) + 15(\text{number of } V) \times 4.2 + 8(\text{number of } P) \times (-1.6) + 1(\text{number of } K) \times (-3.9)\}/40(\text{total number of amino acid residues}) = 1.0.$$

The meniscus regeneration material of the present invention includes the protein (A) having the amino acid sequence described above. Such a material is decomposed by an enzyme in vivo and thus has excellent biodegradability.

The protein (A) in the present invention can be obtained by extraction from natural products or by organic synthesis (e.g., enzymatic method, solid phase synthesis, and liquid phase synthesis) or gene recombination. Examples of the organic synthesis include the method described in "Seikagaku Jikken Koza 1 (Biochemistry Experimental Course 1), Chemistry of protein IV (edited by The Japanese Biochemical Society, published by Tokyo Kagakudojin on Jul. 1, 1981)" or "Zoku Seikagaku Jikken Koza 2) (Sequel to Biochemistry Experimental Course 2, Chemistry of protein (Vol. 2) (edited by The Japanese Biochemical Society, published by Tokyo Kagakudojin on May 20, 1987)." Examples of the gene recombination include the method described in JP 3338441 B. The protein (A) can be produced by extraction from natural products, organic synthesis, and gene recombination. Yet, the gene recombination is preferred for easy alteration of amino acid sequences and mass productivity at low cost.

To enhance the meniscus regeneration ability, the meniscus regeneration material of the present invention preferably includes a meniscus tissue fragment (B).

The meniscus tissue fragment (B) may be obtained by collecting a piece of the meniscus (it may be the meniscus of the patient or the meniscus of a person other than the patient), and finely grinding the meniscus piece.

The meniscus piece can be finely ground with a scalpel, for example.

To enhance the meniscus regeneration ability, the number average volume per fragment of the meniscus tissue fragment (B) is preferably 0.001 to 1,000 $mm^3$, more preferably 0.008 to 970 $mm^3$, particularly preferably 1 to 500 $mm^3$.

In addition to the protein (A) and the meniscus tissue fragment (B), the meniscus regeneration material of the present invention may further include water, an inorganic salt, and/or a phosphoric acid (salt).

Specific examples of the inorganic salt include sodium chloride, potassium chloride, calcium chloride, magnesium chloride, sodium sulfate, potassium sulfate, calcium sulfate, magnesium sulfate, sodium hydrogen carbonate, potassium hydrogen carbonate, calcium hydrogen carbonate, and magnesium hydrogen carbonate. Herein, the inorganic salt does not include phosphoric acids (salts).

To enhance the meniscus regeneration ability, the inorganic salt content (% by weight) of the meniscus regeneration material based on the weight of the meniscus regeneration material is preferably 0 to 3% by weight, more preferably 0 to 1% by weight, particularly preferably 0.001 to 0.5% by weight.

The phosphoric acid (salt) refers to phosphoric acid and/or a phosphate.

Examples of the phosphate include alkali metal salts and alkaline earth metal salts of phosphoric acid. Specific examples include sodium salts, potassium salts, calcium salts, and magnesium salts of phosphoric acid.

To enhance the meniscus regeneration ability, the phosphoric acid (salt) content of the meniscus regeneration material based on the weight of the meniscus regeneration material is preferably 0.001 to 2% by weight, more preferably 0.001 to 0.5% by weight, particularly preferably 0.001 to 0.05% by weight.

To enhance the meniscus regeneration ability, the weight percentage of the protein (A) contained in the meniscus regeneration material of the present invention in the meniscus regeneration material is preferably 5 to 25% by weight, more preferably 10 to 20% by weight.

To enhance the meniscus regeneration ability, the weight percentage of the meniscus tissue fragment (B) contained in the meniscus regeneration material of the present invention in the meniscus regeneration material is preferably 5 to 50% by weight, more preferably 10 to 40% by weight.

To further enhance the meniscus regeneration ability, a ratio of the weight of the protein (A) to the weight of the meniscus tissue fragment (B) (weight of protein (A)/weight of meniscus tissue fragment (B)) in the meniscus regeneration material of the present invention is preferably 0.30 to 0.90, more preferably 0.40 to 0.75.

The meniscus regeneration material of the present invention may be produced by adding the meniscus tissue fragment (B) to an aqueous solution of the protein (A) and mixing them with a pipette, for example. This operation is preferably performed at 4° C. to 10° C. to maintain the cell activity.

For example, the meniscus regeneration material of the present invention may be used as follows:

(1) The meniscus regeneration material of the present invention is warmed to 4° C. to 40° C. (preferably 20° C. to 40° C.) to be a gel.

The meniscus regeneration material gel is administered to a damaged part of the meniscus exposed by incision or the like, thereby promoting the regeneration of the meniscus. After the administration of the meniscus regeneration material, the incision can be sutured and sealed with a collagen membrane, the synovium of the patient, or the like.

(2) The meniscus regeneration material of the present invention is administered to a damaged part of the meniscus under an arthroscope. The meniscus regeneration material is made into a gel by the body temperature of the patient. Thus, as in the above (1), the material can promote the regeneration of the meniscus.

The methods correspond to the therapies of a damaged part of the meniscus of the present invention.

The meniscus regeneration material of the present invention may be used for osteoarthritis, cartilage defect, and meniscus damage (traumatic meniscus damage, etc.), for example.

The use of the meniscus regeneration material for at least one disease selected from the group consisting of osteoarthritis, cartilage defect, and meniscus damage (traumatic meniscus damage) corresponds to the use of the meniscus regeneration material of the present invention.

EXAMPLES

The present invention will be more specifically described below with reference to examples, but the present invention is not limited to the examples.

<Production Example A1: Preparation of SELP8K (A11-2-1(i))>

—Production of SELP8K (A11-2-1(i))

A plasmid pPT0345 encoding SELP8K was prepared by the method described in Examples in JP 4088341 B.

The plasmid was used to transform *Escherichia coli* cells into a strain capable of producing SELP8K. The following describes a method for producing the protein (A) having the sequence (16) using the SELP8K-producing strain.

—Culture of SELP8K-Producing Strain

A culture solution prepared by culturing the SELP8K-producing strain at 30° C. overnight was inoculated to 50 mL of LB medium in a 250 mL flask. Kanamycin was added to a final concentration of 50 mg/mL, and the culture solution was incubated with agitation (200 rpm) at 30° C. When the turbidity (OD 600) of the inoculated culture solution reached 0.8 (measured with spectrophotometer UV1700, Shimadzu Corporation), 40 mL of the culture solution was transferred to another flask pre-warmed at 42° C. and incubated at the same temperature for about two hours. The culture solution was chilled on ice, and the turbidity (OD 600) of the culture solution was measured. *Escherichia coli* cells were collected by centrifugation.

—Purification of SELP8K (A11-2-1(i))

The collected *Escherichia coli* cells were used to purify a protein from an *Escherichia coli* biomass through the following 1 to 7; 1: Lysis, 2: Removal of insoluble cellular debris by centrifugation, 3: Ammonium sulfate precipitation, 4: Ultrafiltration, 5: Anion exchange chromatography, 6: Ultrafiltration, and 7: Lyophilization. Accordingly, a protein (A) in Production Example A1 (SELP8K) that is a purified protein having a molecular mass of about 80 kDa and having the sequence (16) was obtained.

1: Lysis

Deionized water (200 g) was added to 100 g of the collected *Escherichia coli* cells), followed by lysis with a high-pressure homogenizer (55 MPa). Thus, a lysate containing lysed cells was obtained. Subsequently, the pH of the lysate was adjusted to 4.0 with glacial acetic acid.

2: Removal of Insoluble Cellular Debris by Centrifugation

The lysate was further centrifuged (6,300 rpm, 4° C., 30 min) to collect the supernatant.

3: Ammonium Sulfate Precipitation

A saturated ammonium sulfate solution was added to the collected supernatant to give an ammonium sulfate concentration of 25% by weight, followed by standing for 8 to 12 hours. Then, the precipitate was collected by centrifugation. The collected precipitate was dissolved in deionized water. To the solution was added a saturated ammonium sulfate solution to similarly give an ammonium sulfate concentration of 25% by weight, followed by standing for 8 to 12 hours. Then, the precipitate was collected by centrifugation. The collected precipitate was dissolved in deionized water to obtain a solution.

4: Ultrafiltration

The solution prepared in "3: Ammonium sulfate precipitation" was applied to an ultrafilter with a cut-off molecular mass of 30,000 Da (Hollow Fiber, GE Healthcare). The solution prepared in "3: Ammonium sulfate precipitation" was ultrafiltered against deionized water in an amount 10 times the volume of the solution. Thus, the protein was separated by ultrafiltration.

5: Anion Exchange Chromatography

The protein separated by ultrafiltration was dissolved in a 10 mM sodium acetate buffer to a concentration of 20 g/L, and applied to AKTA Prime (GE Healthcare) to which an anion exchange column (Hi PrepSP XL16/10, GE Healthcare) was connected. Then, using 500 mM of a 10 mM sodium acetate buffer as an eluate, an eluted fraction was collected.

6: Ultrafiltration

The solution obtained in "5: Anion exchange chromatography" was treated in the same manner as in "(4) Ultrafiltration" to separate the protein.

7: Lyophilization

The protein was dissolved in deionized water to give a 5 g/L solution. The solution was poured into a stainless-steel vat such that the water level would be 15 mm or lower. The vat was placed in a lyophilizer (NIHON TECHNO SERVICE CO., LTD.) to freeze the solution at −40° C. over 16 hours. The frozen product was subjected to primary drying at a vacuum of 8 Pa or less at −20° C. over 90 hours, and then to secondary drying at a vacuum of 8 Pa or less at 20° C. over 24 hours. Accordingly, a protein (A) in Production Example A1 (SELP8K) was obtained.

—Identification of SELP8K (A11-2-1(i))

The protein (A) in Production Example A1 was identified by the following procedure.

The protein was analyzed by Western Blotting using a rabbit anti-SELP8K antibody and a rabbit anti-6×His antibody (Roland Corporation) against 6×His tag at the C terminal. Western Blotting was performed by the procedure described later. A band exhibiting reactivity with each antibody was found at an apparent molecular mass of 80 kDa.

Table 1 shows the percentages of the amino acid residues (measured values) in the protein (A) in Production Example A1 determined by an amino acid analysis using an amino acid analysis system (Prominence, Shimadzu Corporation) and the percentages of the amino acid residues (theoretical values) in SELP8K estimated from a synthetic gene sequence.

The protein (A) in Production Example A1 was confirmed as a protein (SELP8K) having the sequence (16) including 13 polypeptide chains (Y'2) having a $(GVGVP)_4GKGVP(GVGVP)_3$ sequence (6) and 12 polypeptide chains (S1-1) having an amino acid sequence $(GAGAGS)_4$ (5), where these polypeptide chains are alternately linked by a chemical bond. Here, the polypeptide chain (Y'2) is a polypeptide chain in which one of valines (V) in the polypeptide chain (Y) consisting of 8 tandem repeats of the GVGVP sequence (4) is replaced by a lysine (K) residue, and the amino acid sequence $(GAGAGS)_4$ (5) includes 4 tandem repeats of the GAGAGS sequence (2).

TABLE 1

| Amino acid | Measured value Percentage (%) | Theoretical value Percentage (%) |
|---|---|---|
| Ala | 12.3 | 12.2 |
| Asx | 0.9 | 0.8 |
| Glx | n.d. | 0.4 |
| Phe | 0.4 | 0.1 |
| Gly | 43.7 | 41.5 |
| His | 0.4 | 0.8 |
| Ile | 0.3 | 0 |
| Lys | 1.5 | 1.5 |
| Leu | 0.3 | 0.5 |
| Met | 0.3 | 0.3 |
| Pro | 11.7 | 12.4 |
| Arg | 0.5 | 0.6 |
| Ser | 5.3 | 6.1 |
| Thr | n.d. | 0.1 |
| Val | 21.2 | 22.4 |
| Tyr | 1.1 | 0.1 |

<Western Blotting>

A sample for Western Blotting (20 μL) was mixed with 10 mL of 3×SDS treatment buffer (150 mM Tris HCl (pH 6.8), 300 mM dithiothreitol, 6% dodecyl sodium sulfate (SDS), 0.3% bromophenol blue, and 30% glycerol) and heated at 95° C. for five minutes. Thus, a sample for electrophoresis was prepared. SDS-PAGE was carried out with 15 μL of the sample for electrophoresis. After electrophoresis, the gel was transferred to a polyvinylidene fluoride membrane (hereinafter also simply referred to as "membrane"), and immersed in a blocking buffer (20 mM Tris (pH 7.6), 137 mM NaCl, 0.1% Tween 20, and 5% skimmed milk) with shaking at room temperature for one hour. Thus, the membrane was blocked. After blocking, the membrane was washed with TBS-T (20 mM Tris (pH 7.6), 137 mM NaCl, and 0.1% Tween 20) for two minutes. Next, the membrane was immersed in a solution of a primary antibody (a 1:500 dilution of the primary antibody (anti-SELP8K antibody or anti-His-tag antibody (Rockland Immunochemicals Inc.) in TBS-T), and left to stand at 4° C. overnight for antibody reaction. After the reaction, the membrane was washed for five minutes in TBS-T four times and immersed in a solution of a secondary antibody capable of binding to the primary antibody and containing horseradish peroxidase as a marker enzyme (the solution of the secondary antibody was a 1:2000 dilution of the secondary antibody (ECL anti-rabbit IgG HRP linked F(ab')2 fragment (GE Healthcare)) in TBS-T), and left to stand at room temperature for 30 minutes for antibody reaction. After the reaction, the membrane was washed for five minutes in TBS-T four times, and enzyme reaction was carried out using an ECL-Advance Western Blotting Detection kit (GE Healthcare). A luminometer ForECL (GE Healthcare) was used to expose the membrane to a high speed black and white instant film (Fujifilm Corporation) to visualize bands.

—Determination of Total Percentage of β-Turns and Random Coils

The total percentage of β-turns and random coils in the protein (A) in Production Example A1 was determined as described below.

<Determination of Total Percentage of β-Turns and Random Coils>

The protein (A) in Production Example A1 was dissolved in deionized water (4° C.) to a concentration of 0.3 mg/mL to prepare an aqueous solution of the protein (A) in Production Example A1. The aqueous solution of the protein (A) in Production Example A1 was analyzed at a measurement temperature of 4° C. with a circular dichroism spectrometer (JASCO Corporation: J-820), and a total percentage of β-turns and random coils of the protein (A) was calculated using a secondary structure analysis program (JWSSE model: JASCO Corporation). Table 2 shows the results.

Production Example A2

A protein (A) of Production Example A2 was produced as in Production Example A1, except that a process of "5-2 Refolding (high dilution method)" described below was performed between the processes of "5: Anion exchange chromatography" and "6: Ultrafiltration" in "Purification of SELP8K (A11-2-1(i))" in "Preparation of SELP8K (A11-2-1(i))." Then, the total percentage of β-turns and random coils was determined. Table 2 shows the result.

5-2: Refolding (High Dilution Method)

The eluted fraction from the anion exchange chromatography was mixed with a 10 M urea solution as a protein denaturant to give a 6 M urea solution. The solution was allowed to stand for 12 hours at 4° C. The resulting solution was transferred to a dialysis membrane (Viskase Companies, Inc.) and dialyzed for 12 hours against deionized water in an amount 10 times the volume of the eluted fraction. Subsequently, the deionized water was discarded and replaced with fresh deionized water in an amount 10 times the volume of the eluted fraction to dialyze for another 12 hours. After repeating this operation three more times, i.e., five times in total, the solution in the dialysis membrane was recovered.

Production Example A3

A protein (A) of Production Example A3 was produced as in Production Example A1, except that a process of "5-3 Refolding (high dilution method)" described below was performed between the processes of "5: Anion exchange chromatography" and "6: Ultrafiltration" in "Purification of SELP8K (A11-2-1(i))" in "Preparation of SELP8K (A11-2-1(i))." Then, the total percentage of β-turns and random coils was determined. Table 2 shows the result.

5-3: Refolding (High Dilution Method)

The eluted fraction from the anion exchange chromatography was mixed with a 10 M urea solution as a protein denaturant to give a 6 M urea solution. The solution was allowed to stand for 12 hours at 4° C. The resulting solution

TABLE 2

| | | Amino acid sequence of protein (A) or protein (A') | Total percentage (%) of β-turns and random coils | Ratio of total number of amino acid residues in amino acid sequence (X) and amino acid sequence (X') to the number of all amino acid residues in protein (A) | Ratio of number of GAGAGS sequence (2) to total number of amino acid sequence (X) and amino acid sequence (X') | Hydrophobicity |
|---|---|---|---|---|---|---|
| Production Example | A1 | Sequence of SEQ ID No: 16 | 70.9 | 58.8% | 1:2 | 0.62 |
| | A2 | Sequence of SEQ ID No: 16 | 66.8 | 58.8% | 1:2 | 0.62 |
| | A3 | Sequence of SEQ ID No: 16 | 84.1 | 58.8% | 1:2 | 0.62 |
| | A4 | Sequence of SEQ ID No: 16 | 61.2 | 58.8% | 1:2 | 0.62 |
| | A5 | Sequence of SEQ ID No: 29 | 60.2 | 51.9% | 1:2 | 0.42 |
| Comparative Production Example | A1 | Sequence of SEQ ID No: 16 | 58.1 | 58.8% | 1:2 | 0.62 |
| | A2 | Sequence of SEQ ID No: 16 | 25.5 | 58.8% | 1:2 | 0.62 |
| | A3 | Sequence of SEQ ID No: 16 | 85.6 | 58.8% | 1:2 | 0.62 |
| | A4 | Sequence of SEQ ID No: 27 | 15.4 | 81.3% | — | 1.20 |
| | A5 | Sequence of SEQ ID No: 28 | 62.4 | 20.9% | 3:1 | 0.41 | was transferred to a dialysis membrane (Viskase Companies, Inc.) and dialyzed for 12 hours against deionized water in an amount 10 times the volume of the eluted fraction. Subsequently, the deionized water was discarded and replaced with fresh deionized water in an amount three times the volume of the eluted fraction to dialyze for another 12 hours. After repeating the dialysis of the eluted fraction against deionized water in an amount of three times the volume of the eluted fraction for five more times, the solution in the dialysis membrane was recovered.

Production Example A4

A protein (A) of Production Example A4 was produced as in Production Example A1, except that a process of "5': Affinity chromatography" described below was performed instead of the process of "5: Anion exchange chromatography" in "Purification of SELP8K (A11-2-1(i))" in "Preparation of SELP8K (A11-2-1(i))." Then, the total percentage of R-turns and random coils was determined. Table 2 shows the result.

5': Affinity Chromatography

The protein separated by "4: Ultrafiltration" was purified by affinity chromatography (GE Healthcare, Ni Sepharose 6 Fast Flow) using a His-tag, thereby recovering an eluted fraction.

Production Example A5

A protein (A) of Production Example A5 having a sequence of (29) having a molecular mass of about 30 kDa was produced as in Production Example A1, except that a "plasmid pPT0345-4 encoding SLP8K4" was used instead of the "plasmid pPT0345 encoding SELP8K." Then, the total percentage of β-turns and random coils was determined. Table 2 shows the results.

Comparative Production Example A1

A protein (A') of Comparative Production Example A1 was produced as in Production Example A1, except that a process of "5'': Affinity chromatography" described below was performed instead of the process of "5: Anion exchange chromatography" in "Purification of SELP8K (A11-2-1(i))" in "Preparation of SELP8K (A11-2-1(i))." Then, the total percentage of β-turns and random coils was determined. Table 2 shows the result.

5'': Affinity Chromatography

The protein separated by "4: Ultrafiltration" was purified by affinity chromatography (Clontech, TALON® Single Step Columns) using a His-tag, thereby recovering an eluted fraction.

Comparative Production Example A2

A protein (A') of Comparative Production Example A2 was produced as in Production Example A1, except that the process of "5': Affinity chromatography" was performed without performing the processes of "3: Ammonium sulfate precipitation," "4: Ultrafiltration" and "5: Anion exchange chromatography" in "Purification of SELP8K (A11-2-1(i))" in "Preparation of SELP8K (A11-2-1(i))." Then, the total percentage of β-turns and random coils was determined. Table 2 shows the result.

Comparative Production Example A3

A protein (A') of Comparative Production Example A3 was produced as in Production Example A1, except that the process of "5: Anion exchange chromatography" was not performed in "Purification of SELP8K (A11-2-1(i))" in "Preparation of SELP8K (A11-2-1(i))." Then, the total percentage of β-turns and random coils was determined. Table 2 shows the result.

Comparative Production Example A4

A protein (A') of Comparative Production Example A4 having an amino acid sequence (27) set forth in SEQ ID No: 27 having a molecular mass of about 37 kDa was produced as in Production Example A1, except that a "plasmid pPT0102-2 encoding ELP1.2" was used instead of the "plasmid pPT0345 encoding SELP8K." Then, the total percentage of β-turns and random coils was determined. Table 2 shows the result.

Comparative Production Example A5

A protein (A') of Comparative Production Example A5 having an amino acid sequence (28) set forth in SEQ ID No: 28 having a molecular mass of about 93 kDa was produced as in Production Example A1, except that a "plasmid pSY1398-1 encoding SLP4.1" was used instead of the "plasmid pPT0345 encoding SELP8K." Then, the total percentage of β-turns and random coils was determined. Table 2 shows the result.

Production Example B1: Production of Meniscus Tissue Fragment (B)

A meniscus tissue from a Japanese white rabbit (weight: 3.0 kg) was immobilized on a stage which was preliminarily sterilized in an autoclave.

The immobilized meniscus tissue was cut with a scalpel blade holder provided with scalpel blades arranged in a 200 μm grid pattern. Subsequently, the cut pieces were again cut with the scalpel blade holder into about 200-μm cubical pieces, thereby obtaining meniscus tissue fragments (B) of Production Example B1.

Randomly selected 100 fragments of the meniscus tissue fragments (B) of Production Example B1 were observed with an optical microscope to measure the lengths of the sides of the fragments, and a volume per fragment was calculated. The meniscus tissue fragments (B) of Production Example B1 were found to have a number average volume per fragment of 0.008 mm$^3$.

Production Example B2

Meniscus tissue fragments (B) of Production Example B2, which were cut into about 1,000-μm cubical pieces, were obtained as in Production Example B1, except that the distance between the scalpel blades was changed from 200 μm to 1,000 μm.

Randomly selected 100 fragments of the meniscus tissue fragments (B) of Production Example B2 were observed with an optical microscope to measure the lengths of the sides of the fragments, and a volume per fragment was calculated. The meniscus tissue fragments (B) of Production Example B2 were found to have a number average volume per fragment of 1.141 mm$^3$.

Production Example B3

Meniscus tissue fragments (B) of Production Example B3, which were finely cut into about 9,900-μm cubical pieces, were obtained as in Production Example B1, except that the distance between the scalpel blades was changed from 200 μm to 9,900 μm.

Randomly selected 100 fragments of the meniscus tissue fragments (B) of Production Example B3 were observed with an optical microscope to measure the lengths of the sides of the fragments, and a volume per fragment was calculated. The meniscus tissue fragments (B) of Production Example B3 were found to have a number average volume per fragment of 970 mm$^3$.

Production Example B4

Meniscus tissue fragments (B) of Production Example B4, which were finely cut into about 90-μm cubical pieces, were obtained as in Production Example B1, except that the distance between the scalpel blades was changed from 200 μm to 90 μm.

Randomly selected 100 fragments of the meniscus tissue fragments (B) of Production Example B4 were observed with an optical microscope to measure the lengths of the sides of the fragments, and a volume per fragment was calculated. The meniscus tissue fragments (B) of Production Example B4 were found to have a number average volume per fragment of 0.0007 mm$^3$.

Production Example B5

Meniscus tissue fragments (B) of Production Example B5, which were finely cut into about 10,500-μm cubical pieces, were obtained as in Production Example B1, except that the distance between the scalpel blades was changed from 200 μm to 10,500 μm.

Randomly selected 100 fragments of the meniscus tissue fragments (B) of Production Example B5 were observed with an optical microscope to measure the lengths of the sides of the fragments, and a volume per fragment was calculated. The meniscus tissue fragments (B) of Production Example B5 were found to have a number average volume per fragment of 1,152 mm$^3$.

Examples 1 to 18 and Comparative Examples 1 to 5: Production of Meniscus Regeneration Material and Comparative Meniscus Regeneration Material The protein of each production example or comparative production example and phosphate buffered saline (hereinafter, also simply referred to as PBS, pH 7.2) in amounts (parts by weight) indicated in Table 3 were mixed so that the protein was dissolved in the PBS. The solution and the meniscus tissue fragments of each production example in amounts (parts by weight) indicated in Table 3 were mixed by inversion, thereby producing a meniscus regeneration material of each example or comparative example.

<Meniscus Regeneration Test Using Meniscus Regeneration Material>

The meniscus regeneration material of each example or comparative example was applied to a rabbit meniscus damage model.

Specifically, a knee of an anesthetized Japanese white rabbit (weight: 3.0 kg) was cut open, and a 2 mm-diameter round pillar-shaped defect was formed at an anterior corner of the meniscus.

The meniscus regeneration material was administered to the defect. The cut knee was sutured with a suture.

Four weeks later, the rabbit under sufficiently deep anesthesia was placed in a container filled with carbon dioxide, and cardiopulmonary arrest was confirmed. Next, a tissue including the defect was taken out. The tissue was immersed in 10% buffer formalin to be immobilized with formalin.

The tissue was embedded with paraffin and repeatedly sliced using a microtome (product name: RETORATOME REM-710, Yamato Kohki Industrial Co., Ltd.) in a direction perpendicular to the circular face of the cylindrical defect. Each slice obtained had a cross section having a thickness of about 4 μm.

One of the slices including the center of the circular face of the cylindrical defect was selected as a specimen for evaluations. The specimen was stained with hematoxylin-eosin (Evaluation items 1 and 2) or safranin O (Evaluation item 3). The evaluations were performed by the following methods using a tissue image captured by a digital microscope (VHX-2000, Keyence Corporation).

Evaluation Item 1: Bound Repaired Tissues

The stained defect was observed with an optical microscope for evaluation based on the criteria described below. Three rabbits were tested for the evaluation. The value shown in Table 3 is an average of the scores.

A higher item score indicates higher meniscus regeneration ability.

2: Repaired tissues regenerated from both ends of the cylindrical defect in the cross section of the specimen, and the repaired tissues at the both ends were bound to each other.

1: Repaired tissues regenerated from both ends of the cylindrical defect in the cross section of the specimen, and the repaired tissues at the both ends were not bound to each other.

0: No repaired tissue regenerated from both ends of the cylindrical defect in the cross section of the specimen.

Evaluation Item 2: Presence of Fibrocartilage Cells

The stained defect was observed with an optical microscope for evaluation based on the criteria described below. A higher item score indicates higher meniscus regeneration ability. Three rabbits were tested for the evaluation. The value shown in Table 3 is an average of the scores.

2: Fibrocartilage cells were widely present (the number of fibrocartilage cells per unit area: 2,000 cells/mm$^2$ or more) in the repaired tissues in the cross section of the specimen.

1: Fibrocartilage cells were partly present (the number of fibrocartilage cells per unit area: 100 cells/mm$^2$ or more but less than 2,000 cells/mm$^2$) in the repaired tissues in the cross section of the specimen.

0: No fibrocartilage cells were present (the number of fibrocartilage cells per unit area: less than 100 cells/mm$^2$) in the repaired tissues in the cross section of the specimen.

The "number of fibrocartilage cells per unit area" was determined as follows: The defect of the specimen was observed with a fluorescent microscope (BIOREVO BZ-9000, Keyence Corporation) to count the number of fiber chondrocytes present in a 0.5 mm-square area. The counting was performed at five points including the center and four corners of the defect. The average value was determined as the "number of fibrocartilage cells per unit area."

Evaluation Item 3: Safranin O Staining

The stained defect was observed with an optical microscope for evaluation based on the criteria described below. A higher item score means a larger cartilage substrate production from the fibrocartilage cells and indicates higher meniscus regeneration ability. Three rabbits were tested for the evaluation. The value shown in Table 3 is an average of the scores.

2: The cross section of the specimen was densely stained (staining intensity: 65% or higher).

1: The cross section of the specimen was faintly stained (staining intensity: 33% or higher but lower than 65%).

0: The cross section was not stained (staining intensity: lower than 33% r).

The "staining intensity" was determined as follows: The defect of the specimen was observed with a fluorescent microscope (BIOREVO BZ-9000, Keyence Corporation). The Red/Green/Blue brightness distribution in a 0.5 mm-square area was obtained by histogram analysis. Using the data with a brightness of 150 or higher in the distribution, the percentage (%) of the brightness of red in the sum of the brightnesses of red, green, and blue was calculated (brightness of less than 150 was regarded as brightness 0) The ratio was determined at five points including the center and four corners of the defect. The average value was determined as the "staining intensity."

TABLE 3

| | | Protein (A) or Protein (A') | | PBS | Meniscus tissue fragment (B) | | | |
|---|---|---|---|---|---|---|---|---|
| | | Type | Parts (parts by weight) | Parts (parts by weight) | Type | Parts (parts by weight) | Weight (%) of protein (A) or protein (A') | Weight % of meniscus tissue fragment (B) |
| Example | 1 | Production Example A1 | 12.5 | 62.50 | Production Example B1 | 25.0 | 12.5 | 25.0 |
| | 2 | Production Example A2 | 12.5 | 62.50 | Production Example B1 | 25.0 | 12.5 | 25.0 |
| | 3 | Production Example A3 | 12.5 | 62.50 | Production Example B1 | 25.0 | 12.5 | 25.0 |
| | 4 | Production Example A4 | 12.5 | 62.50 | Production Example B1 | 25.0 | 12.5 | 25.0 |
| | 5 | Production Example A5 | 12.5 | 62.50 | Production Example B1 | 25.0 | 12.5 | 25.0 |
| | 6 | Production Example A1 | 12.5 | 62.50 | Production Example B2 | 25.0 | 12.5 | 25.0 |
| | 7 | Production Example A1 | 12.5 | 62.50 | Production Example B3 | 25.0 | 12.5 | 25.0 |
| | 8 | Production Example A1 | 25.0 | 50.00 | Production Example B1 | 25.0 | 25.0 | 25.0 |
| | 9 | Production Example A1 | 12.5 | 37.50 | Production Example B1 | 50.0 | 12.5 | 50.0 |
| | 10 | Production Example A1 | 5.0 | 70.00 | Production Example B1 | 25.0 | 5.0 | 25.0 |
| | 11 | Production Example A1 | 25.0 | 70.00 | Production Example B1 | 5.0 | 25.0 | 5.0 |
| | 12 | Production Example A1 | 12.5 | 62.50 | Production Example B4 | 25.0 | 12.5 | 25.0 |
| | 13 | Production Example A1 | 12.5 | 62.50 | Production Example B5 | 25.0 | 12.5 | 25.0 |
| | 14 | Production Example A1 | 30.0 | 45.00 | Production Example B1 | 25.0 | 30.0 | 25.0 |
| | 15 | Production Example A1 | 12.5 | 35.00 | Production Example B1 | 52.5 | 12.5 | 52.5 |
| | 16 | Production Example A1 | 4.0 | 71.00 | Production Example B1 | 25.0 | 4.0 | 25.0 |
| | 17 | Production Example A1 | 12.5 | 83.75 | Production Example B1 | 3.8 | 12.5 | 3.8 |
| | 18 | Production Example A1 | 6.3 | 93.75 | — | 0.0 | 6.3 | 0.0 |
| Comparative Example | 1 | Comparative Production Example A1 | 12.5 | 62.50 | Production Example B1 | 25.0 | 12.5 | 25.0 |
| | 2 | Comparative Production Example A2 | 12.5 | 62.50 | Production Example B1 | 25.0 | 12.5 | 25.0 |
| | 3 | Comparative Production Example A3 | 12.5 | 62.50 | Production Example B1 | 25.0 | 12.5 | 25.0 |
| | 4 | Comparative Production Example A4 | 12.5 | 62.50 | Production Example B1 | 25.0 | 12.5 | 25.0 |
| | 5 | Comparative Production Example A5 | 12.5 | 62.50 | Production Example B1 | 25.0 | 12.5 | 25.0 |

| | | Meniscus regeneration test | | | | | | | |
|---|---|---|---|---|---|---|---|---|---|
| | | | Evaluation item 2 | | | | Evaluation item 3 | | |
| | | Evaluation item 1 Score | Score | Measured value of 1st sample (cell/mm$^2$) | Measured value of 2nd sample (cell/mm$^2$) | Measured value of 3rd sample (cell/mm$^2$) | Score | Measured value of 1st sample (%) | Measured value of 2nd sample (%) | Measured value of 3rd sample (%) |
| Example | 1 | 2.0 | 2.0 | 2482 | 2507 | 2461 | 2.0 | 86.8 | 84.7 | 79.5 |
| | 2 | 1.7 | 2.0 | 2398 | 2215 | 2257 | 2.0 | 88.2 | 77.9 | 79.9 |
| | 3 | 2.0 | 2.0 | 2496 | 2372 | 2252 | 2.0 | 85.3 | 84.7 | 78.0 |
| | 4 | 2.0 | 2.0 | 2426 | 2358 | 2206 | 2.0 | 88.4 | 88.3 | 77.3 |
| | 5 | 2.0 | 1.7 | 2097 | 2058 | 1955 | 2.0 | 73.1 | 76.4 | 69.5 |
| | 6 | 2.0 | 2.0 | 2494 | 2510 | 2396 | 1.7 | 81.7 | 75.8 | 64.5 |
| | 7 | 2.0 | 2.0 | 2545 | 2495 | 2310 | 1.7 | 80.8 | 75.2 | 64.0 |
| | 8 | 1.7 | 2.0 | 2357 | 2107 | 2006 | 1.7 | 74.1 | 75.1 | 61.8 |
| | 9 | 1.7 | 2.0 | 2328 | 2234 | 2138 | 1.7 | 70.3 | 75.1 | 63.6 |
| | 10 | 1.7 | 1.7 | 2053 | 2018 | 1869 | 2.0 | 84.8 | 72.6 | 70.6 |
| | 11 | 1.7 | 2.0 | 2107 | 2178 | 2245 | 2.0 | 78.2 | 80.2 | 86.6 |
| | 12 | 1.3 | 1.7 | 2027 | 2050 | 1803 | 1.7 | 70.1 | 73.3 | 58.6 |
| | 13 | 1.3 | 1.7 | 2030 | 2002 | 1748 | 1.3 | 65.2 | 55.2 | 47.6 |
| | 14 | 1.3 | 1.3 | 2020 | 1804 | 1706 | 1.3 | 65.3 | 50.3 | 50.4 |
| | 15 | 1.3 | 1.3 | 2008 | 1801 | 1701 | 1.3 | 66.7 | 50.1 | 50.2 |
| | 16 | 1.7 | 2.0 | 2108 | 2023 | 2019 | 1.3 | 65.4 | 51.2 | 55.4 |
| | 17 | 1.3 | 1.7 | 2007 | 2043 | 1840 | 1.3 | 67.2 | 53.3 | 50.5 |
| | 18 | 1.7 | 1.7 | 2003 | 2003 | 1914 | 1.3 | 65.5 | 59.1 | 50.4 |
| Comparative Example | 1 | 0.7 | 0.3 | 145 | 82 | 43 | 0.3 | 38.1 | 30.1 | 30.8 |
| | 2 | 0.7 | 0.3 | 132 | 73 | 45 | 0.3 | 35.5 | 26.8 | 28.7 |
| | 3 | 0.7 | 0.3 | 166 | 81 | 33 | 0.3 | 39.4 | 21.8 | 24.8 |
| | 4 | 0.3 | 0.3 | 157 | 80 | 33 | 0.3 | 36.2 | 26.2 | 26.6 |
| | 5 | 0.3 | 0.7 | 120 | 123 | 87 | 0.0 | 15.0 | 21.5 | 6.5 |

The evaluation results demonstrate that, in the cases of Examples, regeneration with repaired tissues occurred in the defect, and fibrocartilage cells were widely present in the repaired tissues. These Examples also exhibited good safranin O staining, which occurred at cartilage substrate presumably produced by the fibrocartilage cells.

INDUSTRIAL APPLICABILITY

The meniscus regeneration material of the present invention can promote meniscus regeneration when used to fill a defect of the meniscus of the knee joint and can produce high quality cartilage tissues in the regeneration therapy of damaged meniscus. It is an effective substrate for meniscus regeneration.

SEQUENCE LISTING FREE TEXT

The invention claimed is:
1. A meniscus regeneration material comprising:
a protein (A), and
a meniscus tissue fragment (B),
wherein the protein (A) consists of the amino acid sequence as set forth in SEQ ID NO: 16 or SEQ ID NO: 29; and
wherein the protein (A) has a total percentage of β-turns and random coils of 60% to 85% as determined by circular dichroism spectroscopy.
2. The meniscus regeneration material according to claim 1, wherein the average volume per fragment of the meniscus tissue fragment (B) is 0.001 to 1,000 mm$^3$.
3. The meniscus regeneration material according to claim 1, wherein a weight percentage of the protein (A) in the meniscus regeneration material is 5 to 25% by weight, and a weight percentage of the meniscus tissue fragment (B) in the meniscus regeneration material is 5 to 50% by weight.

* * * * *

```
SEQUENCE LISTING

<160> NUMBER OF SEQ ID NOS: 29

<210> SEQ ID NO 1
<211> LENGTH: 5
<212> TYPE: PRT
<213> ORGANISM: Artificial Sequence
<220> FEATURE:
<223> OTHER INFORMATION: Amino acid sequence(X)

<400> SEQUENCE: 1

Val Pro Gly Val Gly
1               5

<210> SEQ ID NO 2
<211> LENGTH: 6
<212> TYPE: PRT
<213> ORGANISM: Artificial Sequence
<220> FEATURE:
<223> OTHER INFORMATION: Polypeptide chain(S)

<400> SEQUENCE: 2

Gly Ala Gly Ala Gly Ser
1               5

<210> SEQ ID NO 3
<211> LENGTH: 9
<212> TYPE: PRT
<213> ORGANISM: Homo sapiens

<400> SEQUENCE: 3

Gly Ala His Gly Pro Ala Gly Pro Lys
1               5

<210> SEQ ID NO 4
<211> LENGTH: 5
<212> TYPE: PRT
<213> ORGANISM: Homo sapiens

<400> SEQUENCE: 4

Gly Val Gly Val Pro
1               5

<210> SEQ ID NO 5
<211> LENGTH: 24
<212> TYPE: PRT
<213> ORGANISM: Artificial Sequence
<220> FEATURE:
<223> OTHER INFORMATION: Polypeptide chain(S)

<400> SEQUENCE: 5

Gly Ala Gly Ala Gly Ser Gly Ala Gly Ala Gly Ser Gly Ala Gly Ala
1               5                   10                  15

Gly Ser Gly Ala Gly Ala Gly Ser
            20
```

```
<210> SEQ ID NO 6
<211> LENGTH: 40
<212> TYPE: PRT
<213> ORGANISM: Artificial Sequence
<220> FEATURE:
<223> OTHER INFORMATION: Polypeptide chain(Y')

<400> SEQUENCE: 6

Gly Val Gly Val Pro Gly Val Gly Val Pro Gly Val Gly Val Pro Gly
1               5                   10                  15

Val Gly Val Pro Gly Lys Gly Val Pro Gly Val Gly Val Pro Gly Val
            20                  25                  30

Gly Val Pro Gly Val Gly Val Pro
        35                  40

<210> SEQ ID NO 7
<211> LENGTH: 5
<212> TYPE: PRT
<213> ORGANISM: artificial sequence
<220> FEATURE:
<223> OTHER INFORMATION: Amino acid sequence(X')

<400> SEQUENCE: 7

Gly Lys Gly Val Pro
1               5

<210> SEQ ID NO 8
<211> LENGTH: 5
<212> TYPE: PRT
<213> ORGANISM: Artificial Sequence
<220> FEATURE:
<223> OTHER INFORMATION: Amino acid sequence(X')

<400> SEQUENCE: 8

Gly Lys Gly Lys Pro
1               5

<210> SEQ ID NO 9
<211> LENGTH: 5
<212> TYPE: PRT
<213> ORGANISM: artificial sequence
<220> FEATURE:
<223> OTHER INFORMATION: Amino acid sequence(X')

<400> SEQUENCE: 9

Gly Lys Gly Arg Pro
1               5

<210> SEQ ID NO 10
<211> LENGTH: 5
<212> TYPE: PRT
<213> ORGANISM: Artificial Sequence
<220> FEATURE:
<223> OTHER INFORMATION: Amino acid sequence(X')

<400> SEQUENCE: 10

Gly Arg Gly Arg Pro
1               5

<210> SEQ ID NO 11
<211> LENGTH: 5
<212> TYPE: PRT
<213> ORGANISM: Artificial Sequence
<220> FEATURE:
<223> OTHER INFORMATION: Amino acid sequence(Z)
```

<400> SEQUENCE: 11

Val Ala Ala Gly Tyr
1               5

<210> SEQ ID NO 12
<211> LENGTH: 5
<212> TYPE: PRT
<213> ORGANISM: Artificial Sequence
<220> FEATURE:
<223> OTHER INFORMATION: Amino acid sequence(Z)

<400> SEQUENCE: 12

Gly Ala Ala Gly Tyr
1               5

<210> SEQ ID NO 13
<211> LENGTH: 33
<212> TYPE: PRT
<213> ORGANISM: Artificial Sequence
<220> FEATURE:
<223> OTHER INFORMATION: Amino acid sequence(T)

<400> SEQUENCE: 13

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met

<210> SEQ ID NO 14
<211> LENGTH: 40
<212> TYPE: PRT
<213> ORGANISM: Artificial Sequence
<220> FEATURE:
<223> OTHER INFORMATION: Polypeptide chain(Y)

<400> SEQUENCE: 14

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
            20                  25                  30

Gly Val Pro Gly Val Gly Val Pro
            35                  40

<210> SEQ ID NO 15
<211> LENGTH: 12
<212> TYPE: PRT
<213> ORGANISM: Artificial Sequence
<220> FEATURE:
<223> OTHER INFORMATION: Polypeptide chain(S)

<400> SEQUENCE: 15

Gly Ala Gly Ala Gly Ser Gly Ala Gly Ala Gly Ser
1               5                   10

<210> SEQ ID NO 16
<211> LENGTH: 884
<212> TYPE: PRT
<213> ORGANISM: Artificial Sequence
<220> FEATURE:
<223> OTHER INFORMATION: SELP8K

<400> SEQUENCE: 16

```
Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Ala Gly Ser Gly Ala Gly Ala Gly Ser Gly Val Gly Val Pro
            35                  40                  45

Gly Val Gly Val Pro Gly Val Gly Val Pro Gly Val Gly Val Pro Gly
        50                  55                  60

Lys Gly Val Pro Gly Val Gly Val Pro Gly Val Gly Val Pro Gly Val
65                  70                  75                  80

Gly Val Pro Gly Ala Gly Ala Gly Ser Gly Ala Gly Ala Gly Ser Gly
            85                  90                  95

Ala Gly Ala Gly Ser Gly Ala Gly Ala Gly Ser Gly Val Gly Val Pro
            100                 105                 110

Gly Val Gly Val Pro Gly Val Gly Val Pro Gly Val Gly Val Pro Gly
        115                 120                 125

Lys Gly Val Pro Gly Val Gly Val Pro Gly Val Gly Val Pro Gly Val
            130                 135                 140

Gly Val Pro Gly Ala Gly Ala Gly Ser Gly Ala Gly Ala Gly Ser Gly
145                 150                 155                 160

Ala Gly Ala Gly Ser Gly Ala Gly Ala Gly Ser Gly Val Gly Val Pro
            165                 170                 175

Gly Val Gly Val Pro Gly Val Gly Val Pro Gly Val Gly Val Pro Gly
            180                 185                 190

Lys Gly Val Pro Gly Val Gly Val Pro Gly Val Gly Val Pro Gly Val
            195                 200                 205

Gly Val Pro Gly Ala Gly Ala Gly Ser Gly Ala Gly Ala Gly Ser Gly
            210                 215                 220

Ala Gly Ala Gly Ser Gly Ala Gly Ala Gly Ser Gly Val Gly Val Pro
225                 230                 235                 240

Gly Val Gly Val Pro Gly Val Gly Val Pro Gly Val Gly Val Pro Gly
            245                 250                 255

Lys Gly Val Pro Gly Val Gly Val Pro Gly Val Gly Val Pro Gly Val
            260                 265                 270

Gly Val Pro Gly Ala Gly Ala Gly Ser Gly Ala Gly Ala Gly Ser Gly
            275                 280                 285

Ala Gly Ala Gly Ser Gly Ala Gly Ala Gly Ser Gly Val Gly Val Pro
            290                 295                 300

Gly Val Gly Val Pro Gly Val Gly Val Pro Gly Val Gly Val Pro Gly
305                 310                 315                 320

Lys Gly Val Pro Gly Val Gly Val Pro Gly Val Gly Val Pro Gly Val
            325                 330                 335

Gly Val Pro Gly Ala Gly Ala Gly Ser Gly Ala Gly Ala Gly Ser Gly
            340                 345                 350

Ala Gly Ala Gly Ser Gly Ala Gly Ala Gly Ser Gly Val Gly Val Pro
            355                 360                 365

Gly Val Gly Val Pro Gly Val Gly Val Pro Gly Val Gly Val Pro Gly
        370                 375                 380

Lys Gly Val Pro Gly Val Gly Val Pro Gly Val Gly Val Pro Gly Val
385                 390                 395                 400

Gly Val Pro Gly Ala Gly Ala Gly Ser Gly Ala Gly Ala Gly Ser Gly
            405                 410                 415

Ala Gly Ala Gly Ser Gly Ala Gly Ala Gly Ser Gly Val Gly Val Pro
```

```
                420             425             430
Gly Val Gly Val Pro Gly Val Gly Val Pro Gly Val Gly Val Pro Gly
            435                 440             445
Lys Gly Val Pro Gly Val Gly Val Pro Gly Val Gly Val Pro Gly Val
450                 455                 460
Gly Val Pro Gly Ala Gly Ala Gly Ser Gly Ala Gly Ala Gly Ser Gly
465                 470              475                 480
Ala Gly Ala Gly Ser Gly Ala Gly Ala Gly Ser Gly Val Gly Val Pro
                485                 490              495
Gly Val Gly Val Pro Gly Val Gly Val Pro Gly Val Gly Val Pro Gly
            500                 505             510
Lys Gly Val Pro Gly Val Gly Val Pro Gly Val Gly Val Pro Gly Val
            515                 520             525
Gly Val Pro Gly Ala Gly Ala Gly Ser Gly Ala Gly Ala Gly Ser Gly
            530                 535             540
Ala Gly Ala Gly Ser Gly Ala Gly Ala Gly Ser Gly Val Gly Val Pro
545                 550                 555                 560
Gly Val Gly Val Pro Gly Val Gly Val Pro Gly Val Gly Val Pro Gly
                565             570                 575
Lys Gly Val Pro Gly Val Gly Val Pro Gly Val Gly Val Pro Gly Val
            580                 585             590
Gly Val Pro Gly Ala Gly Ala Gly Ser Gly Ala Gly Ala Gly Ser Gly
            595                 600             605
Ala Gly Ala Gly Ser Gly Ala Gly Ala Gly Ser Gly Val Gly Val Pro
610                 615             620
Gly Val Gly Val Pro Gly Val Gly Val Pro Gly Val Gly Val Pro Gly
625                 630             635                 640
Lys Gly Val Pro Gly Val Gly Val Pro Gly Val Gly Val Pro Gly Val
                645             650                 655
Gly Val Pro Gly Ala Gly Ala Gly Ser Gly Ala Gly Ala Gly Ser Gly
                660             665                 670
Ala Gly Ala Gly Ser Gly Ala Gly Ala Gly Ser Gly Val Gly Val Pro
            675                 680             685
Gly Val Gly Val Pro Gly Val Gly Val Pro Gly Val Gly Val Pro Gly
            690                 695             700
Lys Gly Val Pro Gly Val Gly Val Pro Gly Val Gly Val Pro Gly Val
705                 710                 715                 720
Gly Val Pro Gly Ala Gly Ala Gly Ser Gly Ala Gly Ala Gly Ser Gly
                725             730                 735
Ala Gly Ala Gly Ser Gly Ala Gly Ala Gly Ser Gly Val Gly Val Pro
            740                 745             750
Gly Val Gly Val Pro Gly Val Gly Val Pro Gly Val Gly Val Pro Gly
            755                 760             765
Lys Gly Val Pro Gly Val Gly Val Pro Gly Val Gly Val Pro Gly Val
            770                 775             780
Gly Val Pro Gly Ala Gly Ala Gly Ser Gly Ala Gly Ala Gly Ser Gly
785                 790             795                 800
Ala Gly Ala Gly Ser Gly Ala Gly Ala Gly Ser Gly Val Gly Val Pro
                805             810                 815
Gly Val Gly Val Pro Gly Val Gly Val Pro Gly Val Gly Val Pro Gly
            820                 825             830
Lys Gly Val Pro Gly Val Gly Val Pro Gly Val Gly Val Pro Gly Val
            835                 840             845
```

-continued

```
Gly Val Pro Gly Ala Gly Ala Gly Ser Gly Ala Gly Ala Gly Ser Gly
        850                 855                 860

Ala Gly Ala Met Asp Pro Gly Arg Tyr Gln Asp Leu Arg Ser His His
865                 870                 875                 880

His His His His

<210> SEQ ID NO 17
<211> LENGTH: 938
<212> TYPE: PRT
<213> ORGANISM: Artificial Sequence
<220> FEATURE:
<223> OTHER INFORMATION: SELP0K

<400> SEQUENCE: 17

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Ala Gly Ala Gly Ser Gly Ala Gly Ala Gly Ser Gly Val Gly
        35                  40                  45

Val Pro Gly Val Gly Val Pro Gly Val Gly Val Pro Gly Val Gly Val
50                  55                  60

Pro Gly Lys Gly Val Pro Gly Val Gly Val Pro Gly Val Gly Val Pro
65                  70                  75                  80

Gly Val Gly Val Pro Gly Ala Gly Ala Gly Ser Gly Ala Gly Ala Gly
                85                  90                  95

Ser Gly Val Gly Val Pro Gly Val Gly Val Pro Gly Val Gly Val Pro
            100                 105                 110

Gly Val Gly Val Pro Gly Lys Gly Val Pro Gly Val Gly Val Pro Gly
        115                 120                 125

Val Gly Val Pro Gly Val Gly Val Pro Gly Ala Gly Ala Gly Ser Gly
    130                 135                 140

Ala Gly Ala Gly Ser Gly Val Gly Val Pro Gly Val Gly Val Pro Gly
145                 150                 155                 160

Val Gly Val Pro Gly Val Gly Val Pro Gly Lys Gly Val Pro Gly Val
                165                 170                 175

Gly Val Pro Gly Val Gly Val Pro Gly Val Gly Val Pro Gly Ala Gly
            180                 185                 190

Ala Gly Ser Gly Ala Gly Ala Gly Ser Gly Val Gly Val Pro Gly Val
        195                 200                 205

Gly Val Pro Gly Val Gly Val Pro Gly Val Gly Val Pro Gly Lys Gly
    210                 215                 220

Val Pro Gly Val Gly Val Pro Gly Val Gly Val Pro Gly Val Gly Val
225                 230                 235                 240

Pro Gly Ala Gly Ala Gly Ser Gly Ala Gly Ala Gly Ser Gly Val Gly
                245                 250                 255

Val Pro Gly Val Gly Val Pro Gly Val Gly Val Pro Gly Val Gly Val
            260                 265                 270

Pro Gly Lys Gly Val Pro Gly Val Gly Val Pro Gly Val Gly Val Pro
        275                 280                 285

Gly Val Gly Val Pro Gly Ala Gly Ala Gly Ser Gly Ala Gly Ala Gly
    290                 295                 300

Ser Gly Val Gly Val Pro Gly Val Gly Val Pro Gly Val Gly Val Pro
305                 310                 315                 320
```

```
Gly Val Gly Val Pro Gly Lys Gly Val Pro Gly Val Gly Val Pro Gly
                325                 330                 335

Val Gly Val Pro Gly Val Gly Val Pro Gly Ala Gly Ala Gly Ser Gly
            340                 345                 350

Ala Gly Ala Gly Ser Gly Val Gly Val Pro Gly Val Gly Val Pro Gly
        355                 360                 365

Val Gly Val Pro Gly Val Gly Val Pro Gly Lys Gly Val Pro Gly Val
    370                 375                 380

Gly Val Pro Gly Val Gly Val Pro Gly Val Gly Val Pro Gly Ala Gly
385                 390                 395                 400

Ala Gly Ser Gly Ala Gly Ala Gly Ser Gly Val Gly Val Pro Gly Val
            405                 410                 415

Gly Val Pro Gly Val Gly Val Pro Gly Val Gly Val Pro Gly Lys Gly
        420                 425                 430

Val Pro Gly Val Gly Val Pro Gly Val Gly Val Pro Gly Val Gly Val
    435                 440                 445

Pro Gly Ala Gly Ala Gly Ser Gly Ala Gly Ala Gly Ser Gly Val Gly
450                 455                 460

Val Pro Gly Val Gly Val Pro Gly Val Gly Val Pro Gly Val Gly Val
465                 470                 475                 480

Pro Gly Lys Gly Val Pro Gly Val Gly Val Pro Gly Val Gly Val Pro
            485                 490                 495

Gly Val Gly Val Pro Gly Ala Gly Ala Gly Ser Gly Ala Gly Ala Gly
        500                 505                 510

Ser Gly Val Gly Val Pro Gly Val Gly Val Pro Gly Val Gly Val Pro
    515                 520                 525

Gly Val Gly Val Pro Gly Lys Gly Val Pro Gly Val Gly Val Pro Gly
530                 535                 540

Val Gly Val Pro Gly Val Gly Val Pro Gly Ala Gly Ala Gly Ser Gly
545                 550                 555                 560

Ala Gly Ala Gly Ser Gly Val Gly Val Pro Gly Val Gly Val Pro Gly
            565                 570                 575

Val Gly Val Pro Gly Val Gly Val Pro Gly Lys Gly Val Pro Gly Val
        580                 585                 590

Gly Val Pro Gly Val Gly Val Pro Gly Val Gly Val Pro Gly Ala Gly
    595                 600                 605

Ala Gly Ser Gly Ala Gly Ala Gly Ser Gly Val Gly Val Pro Gly Val
610                 615                 620

Gly Val Pro Gly Val Gly Val Pro Gly Val Gly Val Pro Gly Lys Gly
625                 630                 635                 640

Val Pro Gly Val Gly Val Pro Gly Val Gly Val Pro Gly Val Gly Val
            645                 650                 655

Pro Gly Ala Gly Ala Gly Ser Gly Ala Gly Ala Gly Ser Gly Val Gly
        660                 665                 670

Val Pro Gly Val Gly Val Pro Gly Val Gly Val Pro Gly Val Gly Val
    675                 680                 685

Pro Gly Lys Gly Val Pro Gly Val Gly Val Pro Gly Val Gly Val Pro
    690                 695                 700

Gly Val Gly Val Pro Gly Ala Gly Ala Gly Ser Gly Ala Gly Ala Gly
705                 710                 715                 720

Ser Gly Val Gly Val Pro Gly Val Gly Val Pro Gly Val Gly Val Pro
            725                 730                 735

Gly Val Gly Val Pro Gly Lys Gly Val Pro Gly Val Gly Val Pro Gly
```

```
                    740                 745                 750
Val Gly Val Pro Gly Val Gly Val Pro Gly Ala Gly Ala Gly Ser Gly
            755                 760                 765

Ala Gly Ala Gly Ser Gly Val Gly Val Pro Gly Val Gly Val Pro Gly
        770                 775                 780

Val Gly Val Pro Gly Val Gly Val Pro Gly Lys Gly Val Pro Gly Val
785                 790                 795                 800

Gly Val Pro Gly Val Gly Val Pro Gly Val Gly Val Pro Gly Ala Gly
                805                 810                 815

Ala Gly Ser Gly Ala Gly Ala Gly Ser Gly Val Gly Val Pro Gly Val
            820                 825                 830

Gly Val Pro Gly Val Gly Val Pro Gly Val Gly Val Pro Gly Lys Gly
        835                 840                 845

Val Pro Gly Val Gly Val Pro Gly Val Gly Val Pro Gly Val Gly Val
    850                 855                 860

Pro Gly Ala Gly Ala Gly Ser Gly Ala Gly Ala Gly Ser Gly Val Gly
865                 870                 875                 880

Val Pro Gly Val Gly Val Pro Gly Val Gly Val Pro Gly Val Gly Val
                885                 890                 895

Pro Gly Lys Gly Val Pro Gly Val Gly Val Pro Gly Val Gly Val Pro
            900                 905                 910

Gly Val Gly Val Pro Gly Ala Gly Ala Met Asp Pro Gly Arg Tyr Gln
        915                 920                 925

Asp Leu Arg Ser His His His His His His
    930                 935

<210> SEQ ID NO 18
<211> LENGTH: 60
<212> TYPE: PRT
<213> ORGANISM: Artificial Sequence
<220> FEATURE:
<223> OTHER INFORMATION: Polypeptide chain(Y')

<400> SEQUENCE: 18

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Lys
            20                  25                  30

Gly Val Pro Gly Val Gly Val Pro Gly Val Gly Val Pro Gly Val Gly
        35                  40                  45

Val Pro Gly Val Gly Val Pro Gly Val Gly Val Pro
    50                  55                  60

<210> SEQ ID NO 19
<211> LENGTH: 24
<212> TYPE: PRT
<213> ORGANISM: Artificial Sequence
<220> FEATURE:
<223> OTHER INFORMATION: Polypeptide chain(S)

<400> SEQUENCE: 19

Gly Ala Gly Ala Gly Ser Gly Ala Gly Ala Gly Ser Gly Ala Gly Ala
1               5                   10                  15

Gly Ser Gly Ala Gly Ala Gly Ser
            20

<210> SEQ ID NO 20
<211> LENGTH: 1134
```

```
<212> TYPE: PRT
<213> ORGANISM: Artificial Sequence
<220> FEATURE:
<223> OTHER INFORMATION: Protein

<400> SEQUENCE: 20

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Val Gly Val Pro Gly Val Gly Val Pro Gly Val Gly Val Pro
        35                  40                  45

Gly Val Gly Val Pro Gly Val Gly Val Pro Gly Val Gly Val Pro Gly
    50                  55                  60

Lys Gly Val Pro Gly Val Gly Val Pro Gly Val Gly Val Pro Gly Val
65                  70                  75                  80

Gly Val Pro Gly Val Gly Val Pro Gly Val Gly Val Pro Gly Ala Gly
                85                  90                  95

Ala Gly Ser Gly Ala Gly Ala Gly Ser Gly Ala Gly Ala Gly Ser Gly
            100                 105                 110

Ala Gly Ala Gly Ser Gly Val Gly Val Pro Gly Val Gly Val Pro Gly
            115                 120                 125

Val Gly Val Pro Gly Val Gly Val Pro Gly Val Gly Val Pro Gly Val
        130                 135                 140

Gly Val Pro Gly Lys Gly Val Pro Gly Val Gly Val Pro Gly Val Gly
145                 150                 155                 160

Val Pro Gly Val Gly Val Pro Gly Val Gly Val Pro Gly Val Gly Val
                165                 170                 175

Pro Gly Ala Gly Ala Gly Ser Gly Ala Gly Ala Gly Ser Gly Ala Gly
            180                 185                 190

Ala Gly Ser Gly Ala Gly Ala Gly Ser Gly Val Gly Val Pro Gly Val
            195                 200                 205

Gly Val Pro Gly Val Gly Val Pro Gly Val Gly Val Pro Gly Val Gly
        210                 215                 220

Val Pro Gly Val Gly Val Pro Gly Lys Gly Val Pro Gly Val Gly Val
225                 230                 235                 240

Pro Gly Val Gly Val Pro Gly Val Gly Val Pro Gly Val Gly Val Pro
                245                 250                 255

Gly Val Gly Val Pro Gly Ala Gly Ala Gly Ser Gly Ala Gly Ala Gly
            260                 265                 270

Ser Gly Ala Gly Ala Gly Ser Gly Ala Gly Ala Gly Ser Gly Val Gly
            275                 280                 285

Val Pro Gly Val Gly Val Pro Gly Val Gly Val Pro Gly Val Gly Val
        290                 295                 300

Pro Gly Val Gly Val Pro Gly Val Gly Val Pro Gly Lys Gly Val Pro
305                 310                 315                 320

Gly Val Gly Val Pro Gly Val Gly Val Pro Gly Val Gly Val Pro Gly
                325                 330                 335

Val Gly Val Pro Gly Val Gly Val Pro Gly Ala Gly Ala Gly Ser Gly
            340                 345                 350

Ala Gly Ala Gly Ser Gly Ala Gly Ala Gly Ser Gly Ala Gly Ala Gly
            355                 360                 365

Ser Gly Val Gly Val Pro Gly Val Gly Val Pro Gly Val Gly Val Pro
            370                 375                 380
```

```
Gly Val Gly Val Pro Gly Val Gly Val Pro Gly Val Pro Gly
385                 390                 395                 400

Lys Gly Val Pro Gly Val Gly Val Pro Gly Val Gly Val Pro Gly Val
            405                 410                 415

Gly Val Pro Gly Val Gly Val Pro Gly Val Gly Val Pro Gly Ala Gly
            420                 425                 430

Ala Gly Ser Gly Ala Gly Ala Gly Ser Gly Ala Gly Ala Gly Ser Gly
            435                 440                 445

Ala Gly Ala Gly Ser Gly Val Gly Val Pro Gly Val Gly Val Pro Gly
            450                 455                 460

Val Gly Val Pro Gly Val Gly Val Pro Gly Val Gly Val Pro Gly Val
465                 470                 475                 480

Gly Val Pro Gly Lys Gly Val Pro Gly Val Gly Val Pro Gly Val Gly
            485                 490                 495

Val Pro Gly Val Gly Val Pro Gly Val Gly Val Pro Gly Val Gly Val
            500                 505                 510

Pro Gly Ala Gly Ala Gly Ser Gly Ala Gly Ala Gly Ser Gly Ala Gly
            515                 520                 525

Ala Gly Ser Gly Ala Gly Ala Gly Ser Gly Val Gly Val Pro Gly Val
            530                 535                 540

Gly Val Pro Gly Val Gly Val Pro Gly Val Gly Val Pro Gly Val Gly
545                 550                 555                 560

Val Pro Gly Val Gly Val Pro Gly Lys Gly Val Pro Gly Val Gly Val
                    565                 570                 575

Pro Gly Val Gly Val Pro Gly Val Gly Val Pro Gly Val Gly Val Pro
            580                 585                 590

Gly Val Gly Val Pro Gly Ala Gly Ala Gly Ser Gly Ala Gly Ala Gly
            595                 600                 605

Ser Gly Ala Gly Ala Gly Ser Gly Ala Gly Ala Gly Ser Gly Val Gly
            610                 615                 620

Val Pro Gly Val Gly Val Pro Gly Val Gly Val Pro Gly Val Gly Val
625                 630                 635                 640

Pro Gly Val Gly Val Pro Gly Val Gly Val Pro Gly Lys Gly Val Pro
                    645                 650                 655

Gly Val Gly Val Pro Gly Val Gly Val Pro Gly Val Gly Val Pro Gly
            660                 665                 670

Val Gly Val Pro Gly Val Gly Val Pro Gly Ala Gly Ala Gly Ser Gly
            675                 680                 685

Ala Gly Ala Gly Ser Gly Ala Gly Ala Gly Ser Gly Ala Gly Ala Gly
            690                 695                 700

Ser Gly Val Gly Val Pro Gly Val Gly Val Pro Gly Val Gly Val Pro
705                 710                 715                 720

Gly Val Gly Val Pro Gly Val Gly Val Pro Gly Val Gly Val Pro Gly
            725                 730                 735

Lys Gly Val Pro Gly Val Gly Val Pro Gly Val Gly Val Pro Gly Val
            740                 745                 750

Gly Val Pro Gly Val Gly Val Pro Gly Val Gly Val Pro Gly Ala Gly
            755                 760                 765

Ala Gly Ser Gly Ala Gly Ala Gly Ser Gly Ala Gly Ala Gly Ser Gly
            770                 775                 780

Ala Gly Ala Gly Ser Gly Val Gly Val Pro Gly Val Gly Val Pro Gly
            785                 790                 795                 800

Val Gly Val Pro Gly Val Gly Val Pro Gly Val Gly Val Pro Gly Val
```

Gly Val Pro Gly Lys Gly Val Pro Gly Val Gly Val Pro Gly Val Gly
                  820                 825                 830

Val Pro Gly Val Gly Val Pro Gly Val Gly Val Pro Gly Val Gly Val
              835                 840                 845

Pro Gly Ala Gly Ala Gly Ser Gly Ala Gly Ala Gly Ser Gly Ala Gly
  850                 855                 860

Ala Gly Ser Gly Ala Gly Ala Gly Ser Gly Val Gly Val Pro Gly Val
865                 870                 875                 880

Gly Val Pro Gly Val Gly Val Pro Gly Val Gly Val Pro Gly Val Gly
                  885                 890                 895

Val Pro Gly Val Gly Val Pro Gly Lys Gly Val Pro Gly Val Gly Val
              900                 905                 910

Pro Gly Val Gly Val Pro Gly Val Gly Val Pro Gly Val Gly Val Pro
  915                 920                 925

Gly Val Gly Val Pro Gly Ala Gly Ala Gly Ser Gly Ala Gly Ala Gly
                  930                 935                 940

Ser Gly Ala Gly Ala Gly Ser Gly Ala Gly Ala Gly Ser Gly Val Gly
945                 950                 955                 960

Val Pro Gly Val Gly Val Pro Gly Val Gly Val Pro Gly Val Gly Val
              965                 970                 975

Pro Gly Val Gly Val Pro Gly Val Gly Val Pro Gly Lys Gly Val Pro
  980                 985                 990

Gly Val Gly Val Pro Gly Val Gly Val Pro Gly Val Gly Val Pro Gly
                  995                1000                1005

Val Gly Val Pro Gly Val Gly Val Pro Gly Ala Gly Ala Gly Ser
 1010                1015                1020

Gly Ala Gly Ala Gly Ser Gly Ala Gly Ala Gly Ser Gly Ala Gly
 1025                1030                1035

Ala Gly Ser Gly Val Gly Val Pro Gly Val Gly Val Pro Gly Val
 1040                1045                1050

Gly Val Pro Gly Val Gly Val Pro Gly Val Gly Val Pro Gly Val
 1055                1060                1065

Gly Val Pro Gly Lys Gly Val Pro Gly Val Gly Val Pro Gly Val
 1070                1075                1080

Gly Val Pro Gly Val Gly Val Pro Gly Val Gly Val Pro Gly Val
 1085                1090                1095

Gly Val Pro Gly Ala Gly Ala Gly Ser Gly Ala Gly Ala Gly Ser
 1100                1105                1110

Gly Ala Gly Ala Met Asp Pro Gly Arg Tyr Gln Asp Leu Arg Ser
 1115                1120                1125

His His His His His His
 1130

<210> SEQ ID NO 21
<211> LENGTH: 48
<212> TYPE: PRT
<213> ORGANISM: Artificial Sequence
<220> FEATURE:
<223> OTHER INFORMATION: Polypeptide chain(S)

<400> SEQUENCE: 21

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala

```
            20                  25                  30

Gly Ala Gly Ser Gly Ala Gly Ala Gly Ser Gly Ala Gly Ala Gly Ser
        35                  40                  45

<210> SEQ ID NO 22
<211> LENGTH: 200
<212> TYPE: PRT
<213> ORGANISM: Artificial Sequence
<220> FEATURE:
<223> OTHER INFORMATION: Polypeptide chain(Y)

<400> SEQUENCE: 22

Gly Val Gly Val Pro Gly Val Gly Val Pro Gly Val Gly Val Pro Gly
1               5                  10                  15

Val Gly Val Pro Gly Val Gly Val Pro Gly Val Gly Val Pro Gly Val
            20                  25                  30

Gly Val Pro Gly Val Gly Val Pro Gly Val Gly Val Pro Gly Val Gly
        35                  40                  45

Val Pro Gly Val Gly Val Pro Gly Val Gly Val Pro Gly Val Gly Val
    50                  55                  60

Pro Gly Val Gly Val Pro Gly Val Gly Val Pro Gly Val Gly Val Pro
65                  70                  75                  80

Gly Val Gly Val Pro Gly Val Gly Val Pro Gly Val Gly Val Pro Gly
                85                  90                  95

Val Gly Val Pro Gly Val Gly Val Pro Gly Val Gly Val Pro Gly Val
            100                 105                 110

Gly Val Pro Gly Val Gly Val Pro Gly Val Gly Val Pro Gly Val Gly
        115                 120                 125

Val Pro Gly Val Gly Val Pro Gly Val Gly Val Pro Gly Val Gly Val
    130                 135                 140

Pro Gly Val Gly Val Pro Gly Val Gly Val Pro Gly Val Gly Val Pro
145                 150                 155                 160

Gly Val Gly Val Pro Gly Val Gly Val Pro Gly Val Gly Val Pro Gly
                165                 170                 175

Val Gly Val Pro Gly Val Gly Val Pro Gly Val Gly Val Pro Gly Val
            180                 185                 190

Gly Val Pro Gly Val Gly Val Pro
        195                 200

<210> SEQ ID NO 23
<211> LENGTH: 1294
<212> TYPE: PRT
<213> ORGANISM: Artificial Sequence
<220> FEATURE:
<223> OTHER INFORMATION: SELP6.1

<400> SEQUENCE: 23

Met Asp Pro Val Val Leu Gln Arg Arg Asp Trp Glu Asn Pro Gly Val
1               5                  10                  15

Thr Gln Leu Asn Arg Leu Ala Ala His Pro Pro Phe Ala Ser Asp Pro
            20                  25                  30

Met Gly Ala Gly Ala Gly Ser Gly Ala Gly Ala Gly Ser Gly Ala Gly
        35                  40                  45

Ala Gly Ser Gly Ala Gly Ala Gly Ser Gly Ala Gly Ala Gly Ser Gly
    50                  55                  60

Ala Gly Ala Gly Ser Gly Ala Gly Ala Gly Ser Gly Ala Gly Ala Gly
65                  70                  75                  80
```

-continued

```
Ser Gly Val Gly Val Pro Gly Val Gly Val Pro Gly Val Gly Val Pro
                 85                  90                  95

Gly Val Gly Val Pro Gly Val Gly Val Pro Gly Val Gly Val Pro Gly
            100                 105                 110

Val Gly Val Pro Gly Val Gly Val Pro Gly Val Gly Val Pro Gly Val
            115                 120                 125

Gly Val Pro Gly Val Gly Val Pro Gly Val Gly Val Pro Gly Val Gly
            130                 135                 140

Val Pro Gly Val Gly Val Pro Gly Val Gly Val Pro Gly Val Gly Val
145                 150                 155                 160

Pro Gly Val Gly Val Pro Gly Val Gly Val Pro Gly Val Gly Val Pro
                165                 170                 175

Gly Val Gly Val Pro Gly Val Gly Val Pro Gly Val Gly Val Pro Gly
            180                 185                 190

Val Gly Val Pro Gly Val Gly Val Pro Gly Val Gly Val Pro Gly Val
            195                 200                 205

Gly Val Pro Gly Val Gly Val Pro Gly Val Gly Val Pro Gly Val Gly
            210                 215                 220

Val Pro Gly Val Gly Val Pro Gly Val Gly Val Pro Gly Val Gly Val
225                 230                 235                 240

Pro Gly Val Gly Val Pro Gly Val Gly Val Pro Gly Val Gly Val Pro
                245                 250                 255

Gly Val Gly Val Pro Gly Val Gly Val Pro Gly Val Gly Val Pro Gly
            260                 265                 270

Val Gly Val Pro Gly Val Gly Val Pro Gly Ala Gly Ala Gly Ser Gly
            275                 280                 285

Ala Gly Ala Gly Ser Gly Ala Gly Ala Gly Ser Gly Ala Gly Ala Gly
            290                 295                 300

Ser Gly Ala Gly Ala Gly Ser Gly Ala Gly Ala Gly Ser Gly Ala Gly
305                 310                 315                 320

Ala Gly Ser Gly Ala Gly Ala Gly Ser Gly Val Gly Val Pro Gly Val
                325                 330                 335

Gly Val Pro Gly Val Gly Val Pro Gly Val Gly Val Pro Gly Val Gly
            340                 345                 350

Val Pro Gly Val Gly Val Pro Gly Val Gly Val Pro Gly Val Gly Val
            355                 360                 365

Pro Gly Val Gly Val Pro Gly Val Gly Val Pro Gly Val Gly Val Pro
            370                 375                 380

Gly Val Gly Val Pro Gly Val Gly Val Pro Gly Val Gly Val Pro Gly
385                 390                 395                 400

Val Gly Val Pro Gly Val Gly Val Pro Gly Val Gly Val Pro Gly Val
                405                 410                 415

Gly Val Pro Gly Val Gly Val Pro Gly Val Gly Val Pro Gly Val Gly
            420                 425                 430

Val Pro Gly Val Gly Val Pro Gly Val Gly Val Pro Gly Val Gly Val
            435                 440                 445

Pro Gly Val Gly Val Pro Gly Val Gly Val Pro Gly Val Gly Val Pro
            450                 455                 460

Gly Val Gly Val Pro Gly Val Gly Val Pro Gly Val Gly Val Pro Gly
465                 470                 475                 480

Val Gly Val Pro Gly Val Gly Val Pro Gly Val Gly Val Pro Gly Val
                485                 490                 495

Gly Val Pro Gly Val Gly Val Pro Gly Val Gly Val Pro Gly Val Gly
```

-continued

```
                500                 505                 510
Val Pro Gly Val Gly Val Pro Gly Val Gly Val Pro Gly Val Gly Val
            515                 520                 525

Pro Gly Ala Gly Ala Gly Ser Gly Ala Gly Ala Gly Ser Gly Ala Gly
            530                 535                 540

Ala Gly Ser Gly Ala Gly Ala Gly Ser Gly Ala Gly Ala Gly Ser Gly
545                 550                 555                 560

Ala Gly Ala Gly Ser Gly Ala Gly Ala Gly Ser Gly Ala Gly Ala Gly
                565                 570                 575

Ser Gly Val Gly Val Pro Gly Val Gly Val Pro Gly Val Gly Val Pro
            580                 585                 590

Gly Val Gly Val Pro Gly Val Gly Val Pro Gly Val Gly Val Pro Gly
            595                 600                 605

Val Gly Val Pro Gly Val Gly Val Pro Gly Val Gly Val Pro Gly Val
            610                 615                 620

Gly Val Pro Gly Val Gly Val Pro Gly Val Gly Val Pro Gly Val Gly
625                 630                 635                 640

Val Pro Gly Val Gly Val Pro Gly Val Gly Val Pro Gly Val Gly Val
                645                 650                 655

Pro Gly Val Gly Val Pro Gly Val Gly Val Pro Gly Val Gly Val Pro
            660                 665                 670

Gly Val Gly Val Pro Gly Val Gly Val Pro Gly Val Gly Val Pro Gly
            675                 680                 685

Val Gly Val Pro Gly Val Gly Val Pro Gly Val Gly Val Pro Gly Val
            690                 695                 700

Gly Val Pro Gly Val Gly Val Pro Gly Val Gly Val Pro Gly Val Gly
705                 710                 715                 720

Val Pro Gly Val Gly Val Pro Gly Val Gly Val Pro Gly Val Gly Val
                725                 730                 735

Pro Gly Val Gly Val Pro Gly Val Gly Val Pro Gly Val Gly Val Pro
            740                 745                 750

Gly Val Gly Val Pro Gly Val Gly Val Pro Gly Val Gly Val Pro Gly
            755                 760                 765

Val Gly Val Pro Gly Val Gly Val Pro Gly Ala Gly Ala Gly Ser Gly
            770                 775                 780

Ala Gly Ala Gly Ser Gly Ala Gly Ala Gly Ser Gly Ala Gly Ala Gly
785                 790                 795                 800

Ser Gly Ala Gly Ala Gly Ser Gly Ala Gly Ala Gly Ser Gly Ala Gly
                805                 810                 815

Ala Gly Ser Gly Ala Gly Ala Gly Ser Gly Val Gly Val Pro Gly Val
            820                 825                 830

Gly Val Pro Gly Val Gly Val Pro Gly Val Gly Val Pro Gly Val Gly
            835                 840                 845

Val Pro Gly Val Gly Val Pro Gly Val Gly Val Pro Gly Val Gly Val
            850                 855                 860

Pro Gly Val Gly Val Pro Gly Val Gly Val Pro Gly Val Gly Val Pro
865                 870                 875                 880

Gly Val Gly Val Pro Gly Val Gly Val Pro Gly Val Gly Val Pro Gly
                885                 890                 895

Val Gly Val Pro Gly Val Gly Val Pro Gly Val Gly Val Pro Gly Val
            900                 905                 910

Gly Val Pro Gly Val Gly Val Pro Gly Val Gly Val Pro Gly Val Gly
            915                 920                 925
```

Val Pro Gly Val Gly Val Pro Gly Val Gly Val Pro Gly Val Gly Val
            930                 935                 940

Pro Gly Val Gly Val Pro Gly Val Gly Val Pro Gly Val Gly Val Pro
945                 950                 955                 960

Gly Val Gly Val Pro Gly Val Gly Val Pro Gly Val Gly Val Pro Gly
                965                 970                 975

Val Gly Val Pro Gly Val Gly Val Pro Gly Val Gly Val Pro Gly Val
            980                 985                 990

Gly Val Pro Gly Val Gly Val Pro Gly Val Gly Val Pro Gly Val Gly
        995                 1000                1005

Val Pro Gly Val Gly Val Pro Gly Val Gly Val Pro Gly Val Gly
    1010                1015                1020

Val Pro Gly Ala Gly Ala Gly Ser Gly Ala Gly Ala Gly Ser Gly
    1025                1030                1035

Ala Gly Ala Gly Ser Gly Ala Gly Ala Gly Ser Gly Ala Gly Ala
    1040                1045                1050

Gly Ser Gly Ala Gly Ala Gly Ser Gly Ala Gly Ala Gly Ser Gly
    1055                1060                1065

Ala Gly Ala Gly Ser Gly Val Gly Val Pro Gly Val Gly Val Pro
    1070                1075                1080

Gly Val Gly Val Pro Gly Val Gly Val Pro Gly Val Gly Val Pro
    1085                1090                1095

Gly Val Gly Val Pro Gly Val Gly Val Pro Gly Val Gly Val Pro
    1100                1105                1110

Gly Val Gly Val Pro Gly Val Gly Val Pro Gly Val Gly Val Pro
    1115                1120                1125

Gly Val Gly Val Pro Gly Val Gly Val Pro Gly Val Gly Val Pro
    1130                1135                1140

Gly Val Gly Val Pro Gly Val Gly Val Pro Gly Val Gly Val Pro
    1145                1150                1155

Gly Val Gly Val Pro Gly Val Gly Val Pro Gly Val Gly Val Pro
    1160                1165                1170

Gly Val Gly Val Pro Gly Val Gly Val Pro Gly Val Gly Val Pro
    1175                1180                1185

Gly Val Gly Val Pro Gly Val Gly Val Pro Gly Val Gly Val Pro
    1190                1195                1200

Gly Val Gly Val Pro Gly Val Gly Val Pro Gly Val Gly Val Pro
    1205                1210                1215

Gly Val Gly Val Pro Gly Val Gly Val Pro Gly Val Gly Val Pro
    1220                1225                1230

Gly Val Gly Val Pro Gly Val Gly Val Pro Gly Val Gly Val Pro
    1235                1240                1245

Gly Val Gly Val Pro Gly Val Gly Val Pro Gly Val Gly Val Pro
    1250                1255                1260

Gly Val Gly Val Pro Gly Val Gly Val Pro Gly Ala Gly Ala Met
    1265                1270                1275

Asp Pro Gly Arg Tyr Gln Asp Leu Arg Ser His His His His
    1280                1285                1290

His

<210> SEQ ID NO 24
<211> LENGTH: 20
<212> TYPE: PRT

<213> ORGANISM: artificial sequence
<220> FEATURE:
<223> OTHER INFORMATION: Polypeptide chain(Y)

<400> SEQUENCE: 24

Val Pro Gly Val Gly Val Pro Gly Val Gly Val Pro Gly Val Gly Val
1               5                   10                  15

Pro Gly Val Gly
            20

<210> SEQ ID NO 25
<211> LENGTH: 40
<212> TYPE: PRT
<213> ORGANISM: artificial sequence
<220> FEATURE:
<223> OTHER INFORMATION: Polypeptide chain(Y)

<400> SEQUENCE: 25

Val Pro Gly Val Gly Val Pro Gly Val Gly Val Pro Gly Val Gly Val
1               5                   10                  15

Pro Gly Val Gly Val Pro Gly Val Gly Val Pro Gly Val Gly Val Pro
            20                  25                  30

Gly Val Gly Val Pro Gly Val Gly
        35                  40

<210> SEQ ID NO 26
<211> LENGTH: 2694
<212> TYPE: PRT
<213> ORGANISM: artificial sequence
<220> FEATURE:
<223> OTHER INFORMATION: ELP1.1

<400> SEQUENCE: 26

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Val Pro Gly Val Gly Val Pro Gly Val Gly Val Pro Gly Val Gly
        35                  40                  45

Val Pro Gly Val Gly Gly Ala Gly Ala Gly Ser Val Pro Gly Val Gly
    50                  55                  60

Val Pro Gly Val Gly Val Pro Gly Val Gly Val Pro Gly Val Gly Val
65                  70                  75                  80

Pro Gly Val Gly Val Pro Gly Val Gly Val Pro Gly Val Gly Val Pro
                85                  90                  95

Gly Val Gly Val Pro Gly Val Gly Val Pro Gly Val Gly Val Pro Gly
            100                 105                 110

Val Gly Val Pro Gly Val Gly Gly Ala Gly Ala Gly Ser Val Pro Gly
        115                 120                 125

Val Gly Val Pro Gly Val Gly Val Pro Gly Val Gly Val Pro Gly Val
    130                 135                 140

Gly Val Pro Gly Val Gly Val Pro Gly Val Gly Val Pro Gly Val Gly
145                 150                 155                 160

Val Pro Gly Val Gly Val Pro Gly Val Gly Val Pro Gly Val Gly Val
                165                 170                 175

Pro Gly Val Gly Val Pro Gly Val Gly Gly Ala Gly Ala Gly Ser Val
            180                 185                 190

Pro Gly Val Gly Val Pro Gly Val Gly Val Pro Gly Val Gly Val Pro
        195                 200                 205

-continued

```
Gly Val Gly Val Pro Gly Val Gly Val Pro Gly Val Gly Val Pro Gly
    210                 215                 220
Val Gly Val Pro Gly Val Gly Val Pro Gly Val Gly Val Pro Gly Val
225                 230                 235                 240
Gly Val Pro Gly Val Gly Val Pro Gly Val Gly Gly Ala Gly Ala Gly
                245                 250                 255
Ser Val Pro Gly Val Gly Val Pro Gly Val Gly Val Pro Gly Val Gly
            260                 265                 270
Val Pro Gly Val Gly Val Pro Gly Val Gly Val Pro Gly Val Gly Val
        275                 280                 285
Pro Gly Val Gly Val Pro Gly Val Gly Val Pro Gly Val Gly Val Pro
    290                 295                 300
Gly Val Gly Val Pro Gly Val Gly Val Pro Gly Val Gly Gly Ala Gly
305                 310                 315                 320
Ala Gly Ser Val Pro Gly Val Gly Val Pro Gly Val Gly Val Pro Gly
                325                 330                 335
Val Gly Val Pro Gly Val Gly Val Pro Gly Val Gly Val Pro Gly Val
            340                 345                 350
Gly Val Pro Gly Val Gly Val Pro Gly Val Gly Val Pro Gly Val Gly
        355                 360                 365
Val Pro Gly Val Gly Val Pro Gly Val Gly Val Pro Gly Val Gly Gly
    370                 375                 380
Ala Gly Ala Gly Ser Val Pro Gly Val Gly Val Pro Gly Val Gly Val
385                 390                 395                 400
Pro Gly Val Gly Val Pro Gly Val Gly Val Pro Gly Val Gly Val Pro
                405                 410                 415
Gly Val Gly Val Pro Gly Val Gly Val Pro Gly Val Gly Val Pro Gly
            420                 425                 430
Val Gly Val Pro Gly Val Gly Val Pro Gly Val Gly Val Pro Gly Val
        435                 440                 445
Gly Gly Ala Gly Ala Gly Ser Val Pro Gly Val Gly Val Pro Gly Val
    450                 455                 460
Gly Val Pro Gly Val Gly Val Pro Gly Val Gly Val Pro Gly Val Gly
465                 470                 475                 480
Val Pro Gly Val Gly Val Pro Gly Val Gly Val Pro Gly Val Gly Val
                485                 490                 495
Pro Gly Val Gly Val Pro Gly Val Gly Val Pro Gly Val Gly Val Pro
            500                 505                 510
Gly Val Gly Gly Ala Gly Ala Gly Ser Val Pro Gly Val Gly Val Pro
        515                 520                 525
Gly Val Gly Val Pro Gly Val Gly Val Pro Gly Val Gly Val Pro Gly
    530                 535                 540
Val Gly Val Pro Gly Val Gly Val Pro Gly Val Gly Val Pro Gly Val
545                 550                 555                 560
Gly Val Pro Gly Val Gly Val Pro Gly Val Gly Val Pro Gly Val Gly
                565                 570                 575
Val Pro Gly Val Gly Gly Ala Gly Ala Gly Ser Val Pro Gly Val Gly
            580                 585                 590
Val Pro Gly Val Gly Val Pro Gly Val Gly Val Pro Gly Val Gly Val
        595                 600                 605
Pro Gly Val Gly Val Pro Gly Val Gly Val Pro Gly Val Gly Val Pro
    610                 615                 620
```

```
Gly Val Gly Val Pro Gly Val Gly Val Pro Gly Val Gly Val Pro Gly
625                 630                 635                 640

Val Gly Val Pro Gly Val Gly Gly Ala Gly Ala Gly Ser Val Pro Gly
            645                 650                 655

Val Gly Val Pro Gly Val Gly Val Pro Gly Val Gly Val Pro Gly Val
            660                 665                 670

Gly Val Pro Gly Val Gly Val Pro Gly Val Gly Val Pro Gly Val Gly
        675                 680                 685

Val Pro Gly Val Gly Val Pro Gly Val Gly Val Pro Gly Val Gly Val
    690                 695                 700

Pro Gly Val Gly Val Pro Gly Val Gly Gly Ala Gly Ala Gly Ser Val
705                 710                 715                 720

Pro Gly Val Gly Val Pro Gly Val Gly Val Pro Gly Val Gly Val Pro
                725                 730                 735

Gly Val Gly Val Pro Gly Val Gly Val Pro Gly Val Gly Val Pro Gly
            740                 745                 750

Val Gly Val Pro Gly Val Gly Val Pro Gly Val Gly Val Pro Gly Val
            755                 760                 765

Gly Val Pro Gly Val Gly Val Pro Gly Val Gly Gly Ala Gly Ala Gly
        770                 775                 780

Ser Val Pro Gly Val Gly Val Pro Gly Val Gly Val Pro Gly Val Gly
785                 790                 795                 800

Val Pro Gly Val Gly Val Pro Gly Val Gly Val Pro Gly Val Gly Val
                805                 810                 815

Pro Gly Val Gly Val Pro Gly Val Gly Val Pro Gly Val Gly Val Pro
            820                 825                 830

Gly Val Gly Val Pro Gly Val Gly Val Pro Gly Val Gly Gly Ala Gly
        835                 840                 845

Ala Gly Ser Val Pro Gly Val Gly Val Pro Gly Val Gly Val Pro Gly
    850                 855                 860

Val Gly Val Pro Gly Val Gly Val Pro Gly Val Gly Val Pro Gly Val
865                 870                 875                 880

Gly Val Pro Gly Val Gly Val Pro Gly Val Gly Val Pro Gly Val Gly
            885                 890                 895

Val Pro Gly Val Gly Val Pro Gly Val Gly Val Pro Gly Val Gly Gly
            900                 905                 910

Ala Gly Ala Gly Ser Val Pro Gly Val Gly Val Pro Gly Val Gly Val
        915                 920                 925

Pro Gly Val Gly Val Pro Gly Val Gly Val Pro Gly Val Gly Val Pro
    930                 935                 940

Gly Val Gly Val Pro Gly Val Gly Val Pro Gly Val Gly Val Pro Gly
945                 950                 955                 960

Val Gly Val Pro Gly Val Gly Val Pro Gly Val Gly Val Pro Gly Val
            965                 970                 975

Gly Gly Ala Gly Ala Gly Ser Val Pro Gly Val Gly Val Pro Gly Val
        980                 985                 990

Gly Val Pro Gly Val Gly Val Pro  Gly Val Gly Val Pro  Gly Val Gly
        995                 1000                 1005

Val Pro  Gly Val Gly Val Pro  Gly Val Gly Val Pro  Gly Val Gly
    1010                 1015                 1020

Val Pro  Gly Val Gly Val Pro  Gly Val Gly Val Pro  Gly Val Gly
    1025                 1030                 1035

Val Pro  Gly Val Gly Gly Ala  Gly Ala Gly Ser Val  Pro Gly Val
```

```
            1040                1045                1050

Gly Val Pro Gly Val Gly Val Pro Gly Val Gly Val Pro Gly Val
            1055                1060                1065

Gly Val Pro Gly Val Gly Val Pro Gly Val Gly Val Pro Gly Val
            1070                1075                1080

Gly Val Pro Gly Val Gly Val Pro Gly Val Gly Val Pro Gly Val
            1085                1090                1095

Gly Val Pro Gly Val Gly Val Pro Gly Val Gly Gly Ala Gly Ala
            1100                1105                1110

Gly Ser Val Pro Gly Val Gly Val Pro Gly Val Gly Val Pro Gly
            1115                1120                1125

Val Gly Val Pro Gly Val Gly Val Pro Gly Val Gly Val Pro Gly
            1130                1135                1140

Val Gly Val Pro Gly Val Gly Val Pro Gly Val Gly Val Pro Gly
            1145                1150                1155

Val Gly Val Pro Gly Val Gly Val Pro Gly Val Gly Val Pro Gly
            1160                1165                1170

Val Gly Gly Ala Gly Ala Gly Ser Val Pro Gly Val Gly Val Pro
            1175                1180                1185

Gly Val Gly Val Pro Gly Val Gly Val Pro Gly Val Gly Val Pro
            1190                1195                1200

Gly Val Gly Val Pro Gly Val Gly Val Pro Gly Val Gly Val Pro
            1205                1210                1215

Gly Val Gly Val Pro Gly Val Gly Val Pro Gly Val Gly Val Pro
            1220                1225                1230

Gly Val Gly Val Pro Gly Val Gly Gly Ala Gly Ala Gly Ser Val
            1235                1240                1245

Pro Gly Val Gly Val Pro Gly Val Gly Val Pro Gly Val Gly Val
            1250                1255                1260

Pro Gly Val Gly Val Pro Gly Val Gly Val Pro Gly Val Gly Val
            1265                1270                1275

Pro Gly Val Gly Val Pro Gly Val Gly Val Pro Gly Val Gly Val
            1280                1285                1290

Pro Gly Val Gly Val Pro Gly Val Gly Val Pro Gly Val Gly Gly
            1295                1300                1305

Ala Gly Ala Gly Ser Val Pro Gly Val Gly Val Pro Gly Val Gly
            1310                1315                1320

Val Pro Gly Val Gly Val Pro Gly Val Gly Val Pro Gly Val Gly
            1325                1330                1335

Val Pro Gly Val Gly Val Pro Gly Val Gly Val Pro Gly Val Gly
            1340                1345                1350

Val Pro Gly Val Gly Val Pro Gly Val Gly Val Pro Gly Val Gly
            1355                1360                1365

Val Pro Gly Val Gly Gly Ala Gly Ala Gly Ser Val Pro Gly Val
            1370                1375                1380

Gly Val Pro Gly Val Gly Val Pro Gly Val Gly Val Pro Gly Val
            1385                1390                1395

Gly Val Pro Gly Val Gly Val Pro Gly Val Gly Val Pro Gly Val
            1400                1405                1410

Gly Val Pro Gly Val Gly Val Pro Gly Val Gly Val Pro Gly Val
            1415                1420                1425

Gly Val Pro Gly Val Gly Val Pro Gly Val Gly Gly Ala Gly Ala
            1430                1435                1440
```

```
Gly Ser Val Pro Gly Val Gly Val Pro Gly Val Gly Val Pro Gly
    1445             1450                 1455

Val Gly Val Pro Gly Val Gly Val Pro Gly Val Gly Val Pro Gly
    1460             1465                 1470

Val Gly Val Pro Gly Val Gly Val Pro Gly Val Gly Val Pro Gly
    1475             1480                 1485

Val Gly Val Pro Gly Val Gly Val Pro Gly Val Gly Val Pro Gly
    1490             1495                 1500

Val Gly Gly Ala Gly Ala Gly Ser Val Pro Gly Val Gly Val Pro
    1505             1510                 1515

Gly Val Gly Val Pro Gly Val Gly Val Pro Gly Val Gly Val Pro
    1520             1525                 1530

Gly Val Gly Val Pro Gly Val Gly Val Pro Gly Val Gly Val Pro
    1535             1540                 1545

Gly Val Gly Val Pro Gly Val Gly Val Pro Gly Val Gly Val Pro
    1550             1555                 1560

Gly Val Gly Val Pro Gly Val Gly Gly Ala Gly Ala Gly Ser Val
    1565             1570                 1575

Pro Gly Val Gly Val Pro Gly Val Gly Val Pro Gly Val Gly Val
    1580             1585                 1590

Pro Gly Val Gly Val Pro Gly Val Gly Val Pro Gly Val Gly Val
    1595             1600                 1605

Pro Gly Val Gly Val Pro Gly Val Gly Val Pro Gly Val Gly Val
    1610             1615                 1620

Pro Gly Val Gly Val Pro Gly Val Gly Val Pro Gly Val Gly Gly
    1625             1630                 1635

Ala Gly Ala Gly Ser Val Pro Gly Val Gly Val Pro Gly Val Gly
    1640             1645                 1650

Val Pro Gly Val Gly Val Pro Gly Val Gly Val Pro Gly Val Gly
    1655             1660                 1665

Val Pro Gly Val Gly Val Pro Gly Val Gly Val Pro Gly Val Gly
    1670             1675                 1680

Val Pro Gly Val Gly Val Pro Gly Val Gly Val Pro Gly Val Gly
    1685             1690                 1695

Val Pro Gly Val Gly Gly Ala Gly Ala Gly Ser Val Pro Gly Val
    1700             1705                 1710

Gly Val Pro Gly Val Gly Val Pro Gly Val Gly Val Pro Gly Val
    1715             1720                 1725

Gly Val Pro Gly Val Gly Val Pro Gly Val Gly Val Pro Gly Val
    1730             1735                 1740

Gly Val Pro Gly Val Gly Val Pro Gly Val Gly Val Pro Gly Val
    1745             1750                 1755

Gly Val Pro Gly Val Gly Val Pro Gly Val Gly Gly Ala Gly Ala
    1760             1765                 1770

Gly Ser Val Pro Gly Val Gly Val Pro Gly Val Gly Val Pro Gly
    1775             1780                 1785

Val Gly Val Pro Gly Val Gly Val Pro Gly Val Gly Val Pro Gly
    1790             1795                 1800

Val Gly Val Pro Gly Val Gly Val Pro Gly Val Gly Val Pro Gly
    1805             1810                 1815

Val Gly Val Pro Gly Val Gly Val Pro Gly Val Gly Val Pro Gly
    1820             1825                 1830
```

-continued

```
Val Gly Gly Ala Gly Ala Gly Ser Val Pro Gly Val Gly Val Pro
    1835                1840                1845

Gly Val Gly Val Pro Gly Val Gly Val Pro Gly Val Gly Val Pro
    1850                1855                1860

Gly Val Gly Val Pro Gly Val Gly Val Pro Gly Val Gly Val Pro
    1865                1870                1875

Gly Val Gly Val Pro Gly Val Gly Val Pro Gly Val Gly Val Pro
    1880                1885                1890

Gly Val Gly Val Pro Gly Val Gly Gly Ala Gly Ala Gly Ser Val
    1895                1900                1905

Pro Gly Val Gly Val Pro Gly Val Gly Val Pro Gly Val Gly Val
    1910                1915                1920

Pro Gly Val Gly Val Pro Gly Val Gly Val Pro Gly Val Gly Val
    1925                1930                1935

Pro Gly Val Gly Val Pro Gly Val Gly Val Pro Gly Val Gly Val
    1940                1945                1950

Pro Gly Val Gly Val Pro Gly Val Gly Val Pro Gly Val Gly Gly
    1955                1960                1965

Ala Gly Ala Gly Ser Val Pro Gly Val Gly Val Pro Gly Val Gly
    1970                1975                1980

Val Pro Gly Val Gly Val Pro Gly Val Gly Val Pro Gly Val Gly
    1985                1990                1995

Val Pro Gly Val Gly Val Pro Gly Val Gly Val Pro Gly Val Gly
    2000                2005                2010

Val Pro Gly Val Gly Val Pro Gly Val Gly Val Pro Gly Val Gly
    2015                2020                2025

Val Pro Gly Val Gly Gly Ala Gly Ala Gly Ser Val Pro Gly Val
    2030                2035                2040

Gly Val Pro Gly Val Gly Val Pro Gly Val Gly Val Pro Gly Val
    2045                2050                2055

Gly Val Pro Gly Val Gly Val Pro Gly Val Gly Val Pro Gly Val
    2060                2065                2070

Gly Val Pro Gly Val Gly Val Pro Gly Val Gly Val Pro Gly Val
    2075                2080                2085

Gly Val Pro Gly Val Gly Val Pro Gly Val Gly Gly Ala Gly Ala
    2090                2095                2100

Gly Ser Val Pro Gly Val Gly Val Pro Gly Val Gly Val Pro Gly
    2105                2110                2115

Val Gly Val Pro Gly Val Gly Val Pro Gly Val Gly Val Pro Gly
    2120                2125                2130

Val Gly Val Pro Gly Val Gly Val Pro Gly Val Gly Val Pro Gly
    2135                2140                2145

Val Gly Val Pro Gly Val Gly Val Pro Gly Val Gly Val Pro Gly
    2150                2155                2160

Val Gly Gly Ala Gly Ala Gly Ser Val Pro Gly Val Gly Val Pro
    2165                2170                2175

Gly Val Gly Val Pro Gly Val Gly Val Pro Gly Val Gly Val Pro
    2180                2185                2190

Gly Val Gly Val Pro Gly Val Gly Val Pro Gly Val Gly Val Pro
    2195                2200                2205

Gly Val Gly Val Pro Gly Val Gly Val Pro Gly Val Gly Val Pro
    2210                2215                2220

Gly Val Gly Val Pro Gly Val Gly Gly Ala Gly Ala Gly Ser Val
```

-continued

```
            2225                2230                2235

Pro Gly Val Gly Val Pro Gly  Val Gly Val Pro Gly  Val Gly Val
    2240                2245                2250

Pro Gly Val Gly Val Pro Gly  Val Gly Val Pro Gly  Val Gly Val
    2255                2260                2265

Pro Gly Val Gly Val Pro Gly  Val Gly Val Pro Gly  Val Gly Val
    2270                2275                2280

Pro Gly Val Gly Val Pro Gly  Val Gly Val Pro Gly  Val Gly Gly
    2285                2290                2295

Ala Gly Ala Gly Ser Val Pro  Gly Val Gly Val Pro  Gly Val Gly
    2300                2305                2310

Val Pro Gly Val Gly Val Pro  Gly Val Gly Val Pro  Gly Val Gly
    2315                2320                2325

Val Pro Gly Val Gly Val Pro  Gly Val Gly Val Pro  Gly Val Gly
    2330                2335                2340

Val Pro Gly Val Gly Val Pro  Gly Val Gly Val Pro  Gly Val Gly
    2345                2350                2355

Val Pro Gly Val Gly Gly Ala  Gly Ala Gly Ser Val  Pro Gly Val
    2360                2365                2370

Gly Val Pro Gly Val Gly Val  Pro Gly Val Gly Val  Pro Gly Val
    2375                2380                2385

Gly Val Pro Gly Val Gly Val  Pro Gly Val Gly Val  Pro Gly Val
    2390                2395                2400

Gly Val Pro Gly Val Gly Val  Pro Gly Val Gly Val  Pro Gly Val
    2405                2410                2415

Gly Val Pro Gly Val Gly Val  Pro Gly Val Gly Gly  Ala Gly Ala
    2420                2425                2430

Gly Ser Val Pro Gly Val Gly  Val Pro Gly Val Gly  Val Pro Gly
    2435                2440                2445

Val Gly Val Pro Gly Val Gly  Val Pro Gly Val Gly  Val Pro Gly
    2450                2455                2460

Val Gly Val Pro Gly Val Gly  Val Pro Gly Val Gly  Val Pro Gly
    2465                2470                2475

Val Gly Val Pro Gly Val Gly  Val Pro Gly Val Gly  Val Pro Gly
    2480                2485                2490

Val Gly Gly Ala Gly Ala Gly  Ser Val Pro Gly Val  Gly Val Pro
    2495                2500                2505

Gly Val Gly Val Pro Gly Val  Gly Val Pro Gly Val  Gly Val Pro
    2510                2515                2520

Gly Val Gly Val Pro Gly Val  Gly Val Pro Gly Val  Gly Val Pro
    2525                2530                2535

Gly Val Gly Val Pro Gly Val  Gly Val Pro Gly Val  Gly Val Pro
    2540                2545                2550

Gly Val Gly Val Pro Gly Val  Gly Gly Ala Gly Ala  Gly Ser Val
    2555                2560                2565

Pro Gly Val Gly Val Pro Gly  Val Gly Val Pro Gly  Val Gly Val
    2570                2575                2580

Pro Gly Val Gly Val Pro Gly  Val Gly Val Pro Gly  Val Gly Val
    2585                2590                2595

Pro Gly Val Gly Val Pro Gly  Val Gly Val Pro Gly  Val Gly Val
    2600                2605                2610

Pro Gly Val Gly Val Pro Gly  Val Gly Val Pro Gly  Val Gly Gly
    2615                2620                2625
```

Ala Gly Ala Gly Ser Val Pro Gly Val Gly Val Pro Gly Val Gly
         2630                2635                2640

Val Pro Gly Val Gly Val Pro Gly Val Gly Val Pro Gly Val Gly
    2645                2650                2655

Val Pro Gly Val Gly Val Pro Gly Val Gly Val Pro Gly Val Gly
    2660                2665                2670

Gly Ala Gly Ala Met Asp Pro Gly Arg Tyr Gln Asp Leu Arg Ser
    2675                2680                2685

His His His His His His
    2690

<210> SEQ ID NO 27
<211> LENGTH: 494
<212> TYPE: PRT
<213> ORGANISM: Artificial Sequence
<220> FEATURE:
<223> OTHER INFORMATION: ELP1.2

<400> SEQUENCE: 27

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Val Pro Gly Val Gly Val Pro Gly Val Gly Val Pro Gly Val Gly
        35                  40                  45

Val Pro Gly Val Gly Val Val Pro Gly Val Gly Val Pro Gly Val
    50                  55                  60

Gly Val Pro Gly Val Gly Val Pro Gly Val Gly Val Val Pro Gly
65                  70                  75                  80

Val Gly Val Pro Gly Val Gly Val Pro Gly Val Gly Val Pro Gly Val
            85                  90                  95

Gly Val Val Val Pro Gly Val Gly Val Pro Gly Val Gly Val Pro Gly
        100                 105                 110

Val Gly Val Pro Gly Val Gly Val Val Pro Gly Val Gly Val Pro
    115                 120                 125

Gly Val Gly Val Pro Gly Val Gly Val Pro Gly Val Gly Val Val
    130                 135                 140

Pro Gly Val Gly Val Pro Gly Val Gly Val Pro Gly Val Gly Val Pro
145                 150                 155                 160

Gly Val Gly Val Val Pro Gly Val Gly Val Pro Gly Val Gly Val
        165                 170                 175

Pro Gly Val Gly Val Pro Gly Val Gly Val Val Pro Gly Val Gly
    180                 185                 190

Val Pro Gly Val Gly Val Pro Gly Val Gly Val Pro Gly Val Gly Val
            195                 200                 205

Val Val Pro Gly Val Gly Val Pro Gly Val Gly Val Pro Gly Val Gly
        210                 215                 220

Val Pro Gly Val Gly Val Val Pro Gly Val Gly Val Pro Gly Val
225                 230                 235                 240

Gly Val Pro Gly Val Gly Val Pro Gly Val Gly Val Val Pro Gly
            245                 250                 255

Val Gly Val Pro Gly Val Gly Val Pro Gly Val Gly Val Pro Gly Val
        260                 265                 270

Gly Val Val Val Pro Gly Val Gly Val Pro Gly Val Gly Val Pro Gly
    275                 280                 285

```
Val Gly Val Pro Gly Val Gly Val Val Pro Gly Val Gly Val Pro
    290                 295                 300

Gly Val Gly Val Pro Gly Val Gly Val Pro Gly Val Gly Val Val
305                 310                 315                 320

Pro Gly Val Gly Val Pro Gly Val Gly Val Pro Gly Val Gly Val Pro
                325                 330                 335

Gly Val Gly Val Val Pro Gly Val Gly Val Pro Gly Val Gly Val
            340                 345                 350

Pro Gly Val Gly Val Pro Gly Val Gly Val Val Pro Gly Val Gly
            355                 360                 365

Val Pro Gly Val Gly Val Pro Gly Val Gly Val Pro Gly Val Gly Val
    370                 375                 380

Val Val Pro Gly Val Gly Val Pro Gly Val Gly Val Pro Gly Val Gly
385                 390                 395                 400

Val Pro Gly Val Gly Val Val Pro Gly Val Gly Val Pro Gly Val
        405                 410                 415

Gly Val Pro Gly Val Gly Val Pro Gly Val Gly Val Val Pro Gly
            420                 425                 430

Val Gly Val Pro Gly Val Gly Val Pro Gly Val Gly Val Pro Gly Val
    435                 440                 445

Gly Val Val Pro Gly Val Gly Val Pro Gly Val Gly Val Pro Gly
    450                 455                 460

Val Gly Val Pro Gly Val Gly Val Val Gly Ala Gly Ala Met Asp Pro
465                 470                 475                 480

Gly Arg Tyr Gln Asp Leu Arg Ser His His His His His
            485                 490

<210> SEQ ID NO 28
<211> LENGTH: 1388
<212> TYPE: PRT
<213> ORGANISM: Artificial Sequence
<220> FEATURE:
<223> OTHER INFORMATION: SLP4.1

<400> SEQUENCE: 28

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Ala Gly Ala Gly Ser Gly Ala Gly Ala Gly Ser Gly Ala Gly
        35                  40                  45

Ala Gly Ser Gly Ala Gly Ala Gly Ser Gly Ala Gly Ala Gly Ser Gly
50                  55                  60

Ala Gly Ala Gly Ser Gly Val Gly Val Pro Gly Val Gly Val Pro Gly
65                  70                  75                  80

Ala Gly Ala Gly Ser Gly Ala Gly Ala Gly Ser Gly Ala Gly Ala Gly
            85                  90                  95

Ser Gly Ala Gly Ala Gly Ser Gly Ala Gly Ala Gly Ser Gly Ala Gly
            100                 105                 110

Ala Gly Ser Gly Val Gly Val Pro Gly Val Gly Val Pro Gly Ala Gly
        115                 120                 125

Ala Gly Ser Gly Ala Gly Ala Gly Ser Gly Ala Gly Ala Gly Ser Gly
    130                 135                 140

Ala Gly Ala Gly Ser Gly Ala Gly Ala Gly Ser Gly Ala Gly Ala Gly
145                 150                 155                 160
```

```
Ser Gly Val Gly Val Pro Gly Val Gly Val Pro Gly Ala Gly Ala Gly
            165                 170                 175

Ser Gly Ala Gly Ala Gly Ser Gly Ala Gly Ala Gly Ser Gly Ala Gly
            180                 185                 190

Ala Gly Ser Gly Ala Gly Ala Gly Ser Gly Ala Gly Ala Gly Ser Gly
            195                 200                 205

Val Gly Val Pro Gly Val Gly Val Pro Gly Ala Gly Ala Gly Ser Gly
            210                 215                 220

Ala Gly Ala Gly Ser Gly Ala Gly Ala Gly Ser Gly Ala Gly Ala Gly
225                 230                 235                 240

Ser Gly Ala Gly Ala Gly Ser Gly Ala Gly Ala Gly Ser Gly Val Gly
            245                 250                 255

Val Pro Gly Val Gly Val Pro Gly Ala Gly Ala Gly Ser Gly Ala Gly
            260                 265                 270

Ala Gly Ser Gly Ala Gly Ala Gly Ser Gly Ala Gly Ala Gly Ser Gly
            275                 280                 285

Ala Gly Ala Gly Ser Gly Ala Gly Ala Gly Ser Gly Val Gly Val Pro
            290                 295                 300

Gly Val Gly Val Pro Gly Ala Gly Ala Gly Ser Gly Ala Gly Ala Gly
305                 310                 315                 320

Ser Gly Ala Gly Ala Gly Ser Gly Ala Gly Ala Gly Ser Gly Ala Gly
            325                 330                 335

Ala Gly Ser Gly Ala Gly Ala Gly Ser Gly Val Gly Val Pro Gly Val
            340                 345                 350

Gly Val Pro Gly Ala Gly Ala Gly Ser Gly Ala Gly Ala Gly Ser Gly
            355                 360                 365

Ala Gly Ala Gly Ser Gly Ala Gly Ala Gly Ser Gly Ala Gly Ala Gly
            370                 375                 380

Ser Gly Ala Gly Ala Gly Ser Gly Val Gly Val Pro Gly Val Gly Val
385                 390                 395                 400

Pro Gly Ala Gly Ala Gly Ser Gly Ala Gly Ala Gly Ser Gly Ala Gly
            405                 410                 415

Ala Gly Ser Gly Ala Gly Ala Gly Ser Gly Ala Gly Ala Gly Ser Gly
            420                 425                 430

Ala Gly Ala Gly Ser Gly Val Gly Val Pro Gly Val Gly Val Pro Gly
            435                 440                 445

Ala Gly Ala Gly Ser Gly Ala Gly Ala Gly Ser Gly Ala Gly Ala Gly
450                 455                 460

Ser Gly Ala Gly Ala Gly Ser Gly Ala Gly Ala Gly Ser Gly Ala Gly
465                 470                 475                 480

Ala Gly Ser Gly Val Gly Val Pro Gly Val Gly Val Pro Gly Ala Gly
            485                 490                 495

Ala Gly Ser Gly Ala Gly Ala Gly Ser Gly Ala Gly Ala Gly Ser Gly
            500                 505                 510

Ala Gly Ala Gly Ser Gly Ala Gly Ala Gly Ser Gly Ala Gly Ala Gly
            515                 520                 525

Ser Gly Val Gly Val Pro Gly Val Gly Val Pro Gly Ala Gly Ala Gly
            530                 535                 540

Ser Gly Ala Gly Ala Gly Ser Gly Ala Gly Ala Gly Ser Gly Ala Gly
545                 550                 555                 560

Ala Gly Ser Gly Ala Gly Ala Gly Ser Gly Ala Gly Ala Gly Ser Gly
            565                 570                 575
```

```
Val Gly Val Pro Gly Val Gly Val Pro Gly Ala Gly Ala Gly Ser Gly
            580             585             590

Ala Gly Ala Gly Ser Gly Ala Gly Ala Gly Ser Gly Ala Gly Ala Gly
        595             600             605

Ser Gly Ala Gly Ala Gly Ser Gly Ala Gly Ala Gly Ser Gly Val Gly
    610             615             620

Val Pro Gly Val Gly Val Pro Gly Ala Gly Ala Gly Ser Gly Ala Gly
625             630             635             640

Ala Gly Ser Gly Ala Gly Ala Gly Ser Gly Ala Gly Ala Gly Ser Gly
        645             650             655

Ala Gly Ala Gly Ser Gly Ala Gly Ala Gly Ser Gly Val Gly Val Pro
    660             665             670

Gly Val Gly Val Pro Gly Ala Gly Ala Gly Ser Gly Ala Gly Ala Gly
        675             680             685

Ser Gly Ala Gly Ala Gly Ser Gly Ala Gly Ala Gly Ser Gly Ala Gly
    690             695             700

Ala Gly Ser Gly Ala Gly Ala Gly Ser Gly Val Gly Val Pro Gly Val
705             710             715             720

Gly Val Pro Gly Ala Gly Ala Gly Ser Gly Ala Gly Ala Gly Ser Gly
        725             730             735

Ala Gly Ala Gly Ser Gly Ala Gly Ala Gly Ser Gly Ala Gly Ala Gly
    740             745             750

Ser Gly Ala Gly Ala Gly Ser Gly Val Gly Val Pro Gly Val Gly Val
    755             760             765

Pro Gly Ala Gly Ala Gly Ser Gly Ala Gly Ala Gly Ser Gly Ala Gly
    770             775             780

Ala Gly Ser Gly Ala Gly Ala Gly Ser Gly Ala Gly Ala Gly Ser Gly
785             790             795             800

Ala Gly Ala Gly Ser Gly Val Gly Val Pro Gly Val Gly Val Pro Gly
        805             810             815

Ala Gly Ala Gly Ser Gly Ala Gly Ala Gly Ser Gly Ala Gly Ala Gly
    820             825             830

Ser Gly Ala Gly Ala Gly Ser Gly Ala Gly Ala Gly Ser Gly Ala Gly
    835             840             845

Ala Gly Ser Gly Val Gly Val Pro Gly Val Gly Val Pro Gly Ala Gly
850             855             860

Ala Gly Ser Gly Ala Gly Ala Gly Ser Gly Ala Gly Ala Gly Ser Gly
865             870             875             880

Ala Gly Ala Gly Ser Gly Ala Gly Ala Gly Ser Gly Ala Gly Ala Gly
        885             890             895

Ser Gly Val Gly Val Pro Gly Val Gly Val Pro Gly Ala Gly Ala Gly
        900             905             910

Ser Gly Ala Gly Ala Gly Ser Gly Ala Gly Ala Gly Ser Gly Ala Gly
    915             920             925

Ala Gly Ser Gly Ala Gly Ala Gly Ser Gly Ala Gly Ala Gly Ser Gly
    930             935             940

Val Gly Val Pro Gly Val Gly Val Pro Gly Ala Gly Ala Gly Ser Gly
945             950             955             960

Ala Gly Ala Gly Ser Gly Ala Gly Ala Gly Ser Gly Ala Gly Ala Gly
        965             970             975

Ser Gly Ala Gly Ala Gly Ser Gly Ala Gly Ala Gly Ser Gly Val Gly
        980             985             990
```

```
Val Pro Gly Val Gly Val Pro Gly Ala Gly Ala Gly Ser Gly Ala Gly
    995                 1000                1005

Ala Gly Ser Gly Ala Gly Ala Gly Ser Gly Ala Gly Ala Gly Ser
    1010            1015                1020

Gly Ala Gly Ala Gly Ser Gly Ala Gly Ala Gly Ser Gly Val Gly
    1025                1030                1035

Val Pro Gly Val Gly Val Pro Gly Ala Gly Ala Gly Ser Gly Ala
    1040                1045                1050

Gly Ala Gly Ser Gly Ala Gly Ala Gly Ser Gly Ala Gly Ala Gly
    1055                1060                1065

Ser Gly Ala Gly Ala Gly Ser Gly Ala Gly Ala Gly Ser Gly Val
    1070                1075                1080

Gly Val Pro Gly Val Gly Val Pro Gly Ala Gly Ala Gly Ser Gly
    1085                1090                1095

Ala Gly Ala Gly Ser Gly Ala Gly Ala Gly Ser Gly Ala Gly Ala
    1100                1105                1110

Gly Ser Gly Ala Gly Ala Gly Ser Gly Ala Gly Ala Gly Ser Gly
    1115                1120                1125

Val Gly Val Pro Gly Val Gly Val Pro Gly Ala Gly Ala Gly Ser
    1130                1135                1140

Gly Ala Gly Ala Gly Ser Gly Ala Gly Ala Gly Ser Gly Ala Gly
    1145                1150                1155

Ala Gly Ser Gly Ala Gly Ala Gly Ser Gly Ala Gly Ala Gly Ser
    1160                1165                1170

Gly Val Gly Val Pro Gly Val Gly Val Pro Gly Ala Gly Ala Gly
    1175                1180                1185

Ser Gly Ala Gly Ala Gly Ser Gly Ala Gly Ala Gly Ser Gly Ala
    1190                1195                1200

Gly Ala Gly Ser Gly Ala Gly Ala Gly Ser Gly Ala Gly Ala Gly
    1205                1210                1215

Ser Gly Val Gly Val Pro Gly Val Gly Val Pro Gly Ala Gly Ala
    1220                1225                1230

Gly Ser Gly Ala Gly Ala Gly Ser Gly Ala Gly Ala Gly Ser Gly
    1235                1240                1245

Ala Gly Ala Gly Ser Gly Ala Gly Ala Gly Ser Gly Ala Gly Ala
    1250                1255                1260

Gly Ser Gly Val Gly Val Pro Gly Val Gly Val Pro Gly Ala Gly
    1265                1270                1275

Ala Gly Ser Gly Ala Gly Ala Gly Ser Gly Ala Gly Ala Gly Ser
    1280                1285                1290

Gly Ala Gly Ala Gly Ser Gly Ala Gly Ala Gly Ser Gly Ala Gly
    1295                1300                1305

Ala Gly Ser Gly Val Gly Val Pro Gly Val Gly Val Pro Gly Ala
    1310                1315                1320

Gly Ala Gly Ser Gly Ala Gly Ala Gly Ser Gly Ala Gly Ala Gly
    1325                1330                1335

Ser Gly Ala Gly Ala Gly Ser Gly Ala Gly Ala Gly Ser Gly Ala
    1340                1345                1350

Gly Ala Gly Ser Gly Val Gly Val Pro Gly Val Gly Val Pro Gly
    1355                1360                1365

Ala Gly Ala Met Asp Pro Gly Arg Tyr Gln Asp Leu Arg Ser His
    1370                1375                1380
```

His His His His His
    1385

<210> SEQ ID NO 29
<211> LENGTH: 310
<212> TYPE: PRT
<213> ORGANISM: Artificial Sequence
<220> FEATURE:
<223> OTHER INFORMATION: SELP8K4

<400> SEQUENCE: 29

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Val Gly Val Pro Gly Val Gly Val Pro Gly Val Gly Val Pro
        35                  40                  45

Gly Val Gly Val Pro Gly Lys Gly Val Pro Gly Val Gly Val Pro Gly
    50                  55                  60

Val Gly Val Pro Gly Val Gly Val Pro Gly Ala Gly Ala Gly Ser Gly
65                  70                  75                  80

Ala Gly Ala Gly Ser Gly Ala Gly Ala Gly Ser Gly Ala Gly Ala Gly
                85                  90                  95

Ser Gly Val Gly Val Pro Gly Val Gly Val Pro Gly Val Gly Val Pro
            100                 105                 110

Gly Val Gly Val Pro Gly Lys Gly Val Pro Gly Val Gly Val Pro Gly
        115                 120                 125

Val Gly Val Pro Gly Val Gly Val Pro Gly Ala Gly Ala Gly Ser Gly
    130                 135                 140

Ala Gly Ala Gly Ser Gly Ala Gly Ala Gly Ser Gly Ala Gly Ala Gly
145                 150                 155                 160

Ser Gly Val Gly Val Pro Gly Val Gly Val Pro Gly Val Gly Val Pro
                165                 170                 175

Gly Val Gly Val Pro Gly Lys Gly Val Pro Gly Val Gly Val Pro Gly
            180                 185                 190

Val Gly Val Pro Gly Val Gly Val Pro Gly Ala Gly Ala Gly Ser Gly
        195                 200                 205

Ala Gly Ala Gly Ser Gly Ala Gly Ala Gly Ser Gly Ala Gly Ala Gly
    210                 215                 220

Ser Gly Val Gly Val Pro Gly Val Gly Val Pro Gly Val Gly Val Pro
225                 230                 235                 240

Gly Val Gly Val Pro Gly Lys Gly Val Pro Gly Val Gly Val Pro Gly
                245                 250                 255

Val Gly Val Pro Gly Val Gly Val Pro Gly Ala Gly Ala Gly Ser Gly
            260                 265                 270

Ala Gly Ala Gly Ser Gly Ala Gly Ala Gly Ser Gly Ala Gly Ala Gly
        275                 280                 285

Ser Gly Ala Gly Ala Met Asp Pro Gly Arg Tyr Gln Asp Leu Arg Ser
    290                 295                 300

His His His His His His
305                 310